(12) United States Patent
Darzynkiewicz et al.

(10) Patent No.: US 6,821,740 B2
(45) Date of Patent: *Nov. 23, 2004

(54) FLOW CYTOMETRIC METHODS FOR THE CONCURRENT DETECTION OF DISCRETE FUNCTIONAL CONFORMATIONS OF PRB IN SINGLE CELLS

(75) Inventors: Zbigniew Darzynkiewicz, Chappaque, NY (US); Frank Traganos, New York, NY (US); Gloria Juan, Sleepy Hollow, NY (US); Stefan Gruenwald, Encinitas, CA (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 61 days.

(21) Appl. No.: 09/256,817

(22) Filed: Feb. 24, 1999

(65) Prior Publication Data
US 2003/0108952 A1 Jun. 12, 2003

Related U.S. Application Data
(60) Provisional application No. 60/075,908, filed on Feb. 25, 1998.

(51) Int. Cl.[7] ............................................. G01N 33/574
(52) U.S. Cl. ...................... 435/7.2; 435/7.21; 435/7.23; 435/7.24; 435/7.4; 436/800
(58) Field of Search ................................ 435/7.92, 7.4, 435/973, 7.2, 7.21, 7.24, 7.23; 530/388.26, 387.7, 388.2, 388.8, 388.85; 436/850

(56) References Cited

U.S. PATENT DOCUMENTS

| | | | |
|---|---|---|---|
| 5,223,408 A | 6/1993 | Goeddel et al. | 435/69.3 |
| 5,620,842 A | 4/1997 | Davis et al. | 435/4 |
| 5,817,469 A * | 10/1998 | Hubner-Parajsz | 435/7.4 |
| 6,200,766 B1 * | 3/2001 | Davis | 435/7.24 |

OTHER PUBLICATIONS

Volm, M., et al., Prognostic implications of cyclins (D1, E, A), cyclin–dependent kinases (CDK2, CDK4) and tumor-suppressor genes (pRb, p16INK4A) in childhood acute lymphoblastic leukemia. Int. J. Cancer (Pred. Oncol.) 74:508–512.*

Waggoner, A.S. PE–CY5: A new fluorescent antibody label for three–color flow cytometry with a single laser. Ann. New York Acad. Sci. 677:185–193.*

"Antibodies to Retinoblastoma Protein (Rb)," *1998 Research Products Catalog*, PharMingen, 626–632.

Bartek, J. et al., "The Retinoblastoma Protein Pathway and the Restriction Point," *Current Opinion in Cell Biology*, 8(6):805–814 (1996).

Brown, P.O. et al., "Exploring The New World of the Genome with DNA Microarrays," *Nature Genetics Supplement*, 21:33–37 (1999).

Clatch, R.J. et al., "Five–Color Immunophenotyping Plus DNA Content Analysis by Laser Scanning Cytometry," *Cytometry*, 34:36–38 (1998).

Cole, K.A. et al., "The Genetics of Cancer—a 3D Model," *Nature Genetics Supplement*, 21:38–41 (1999).

Darzynkiewicz, Z., "Mammalian Cell–Cycle Analysis," *The Cell Cycle: A Practical Approach*, Fantes, P. et al. (eds.), Oxford University Press, Oxford, United Kingdom, 45–68 (1993).

Darzynkiewicz, Z. et al., "Analysis of DNA Content and Cyclin Protein Expression in Studies of DNA Ploidy, Growth Fraction, Lymphocyte Stimulation, and the Cell Cycle," *Methods in Cell Biology*, Darzynkiewicz, Z. et al. (eds.), Academic Press, 41:421–435 (1994).

de Saint-Vis, B. et al., "The Cytokine Profile Expressed by Human Dendritic Cells Is Dependent on Cell Subtype and Mode of Activation," *J. Immunol.*, 160:1666–1676 (1998).

Debouck, C. et al., "DNA Microarrays in Drug Discovery and Development," *Nature Genetics* Supplement, 21:48–50 (1999).

Deka, C. et al., "Analysis of Fluorescence Lifetime and Quenching of FITC–Conjugated Antibodies on Cells by Phase–Sensitive Flow Cytometry," *Cytometry*, 25:271–279 (1996).

Dowdy, S.F. et al., "Physical Interaction of the Retinoblastoma Protein with Human D Cyclins," *Cell*, 73(3):499–511 (1993).

Duggan, D.J. et al., "Expression Profiling Using cDNA Microarrays," *Nature Genetics Supplement*, 21:10–14 (1999).

Dunaief, J.L. et al., "The Retinoblastoma Protein and BRG1 Form a Complex and Cooperate to Induce Cell Cycle Arrest," *Cell*, 79:119–130 (1994).

Ghanekar, S. et al., "Cytokine Expression by Human Peripheral Blood Dendritic Cells Stimulated In Vitro with HIV–1 and Herpes Simplex Virus," *J. Immunol.*, 157(9):4028–4036 (1996).

(List continued on next page.)

*Primary Examiner*—David Saunders
(74) *Attorney, Agent, or Firm*—Douglas A. Petry

(57) ABSTRACT

Methods, reagents, and kits are provided that permit flow cytometric determination of the phosphorylation status of retinoblastoma susceptibility gene protein (pRB) in individual cells. Methods are described that permit the hypophosphorylated, active, form of pRB to be measured either as an absolute quantity or as a proportion of total cellular pRB. Further described are methods that permit pRB phosphorylation status to be correlated with cell cycle phase and with protein components of the cell cycle. Screening of chemical compounds for antiproliferative and antineoplastic activity using the flow cytometric assays is demonstrated. Reagent kits that facilitate the subject methods are also provided.

37 Claims, 16 Drawing Sheets

OTHER PUBLICATIONS

Gong, J. et al., "Growth Imbalance and Altered Expression of Cyclins B1, A, E, and D3 in MOLT–4 Cells Synchronized in the Cell Cycle by Inhibitors of DNA Replication," *Cell Growth & Differentiation*, 6(11):1485–1493 (1995).

Gong, J. et al., "Expression of Cyclins A, D2 and D3 in Individual Normal Mitogen Stimulated Lymphocytes and in MOLT–4 Leukemic Cells Analyzed by Multiparameter Flow Cytometry," *Leukemia*, 9(5):893–899 (1995).

Juan, G. et al., "Detection of Cyclins in Individual Cells by Flow and Laser Scanning Cytometry," *Methods in Molecular Biology, Flow Cytometry Protocols*, Jaroszeski, M.J. et al. (eds.), Humana Press, New Jersey, 91:67–75 (1996).

Juan, G. et al., "Unscheduled Expression of Cyclins D1 and D3 in Human Tumour Cell Lines," *Cell Proliferation*, 29(5):259–266 (1996).

Juan, G. et al., "DNA Segments Sensitive to Single–Strand–Specific Nucleases Are Present in Chromatin of Mitotic Cells," *Experimental Cell Research*, Ringertz, N.(ed.), Academic Press, 227:197–202 (1996).

Juan, G. et al., "Phosphorylation of Retinoblastoma Protein Assayed in Individual HL–60 Cells during Their Proliferation and Differentiation," *Exp. Cell Res.*, 244:83–92 (1998).

Juan, G. et al., "Phosphorylation of Retinoblastoma Protein (pRb) Assayed in Individual Cells by Multilaser Flow Cytometry," *Clinical Immunol. Newsletter*, 18(9):89–94 (1998).

Juan, G. et al., "Phosphorylation of Retinoblastoma Susceptibility Gene Protein Assayed in Individual Lymphocytes during Their Mitogenic Stimulation," *Exp. Cell Res.*, 239:104–110 (1998).

Juan, G. et al., "$G_1$ Arrest of U937 Cells by Onconase is Associated with Supression of Cyclin D3 Expression, Induction of $p16^{INK4A}$, $p21^{WAF1/CIP1}$ and $p27^{KIP}$ and Decreased pRb Phosphorylation," Leukemia, 12:1241–1248 (1998).

Juan, G. et al., "In Situ DNA Strand Break Labeling for Analysis of Apoptosis and Cell Proliferation by Flow and Laser Scanning Cytometry," *Cell Biology*, 2nd Edition, Celis, J.E. (ed.), Academic Press, 1:341–350 (1998).

Juan, G. et al., Cell Cycle Analysis by Flow and Laser Scanning Cytometry, *Cell Biology*, 2nd Edition, Celis, J.E. (ed.), Academic Press, 1:261–274 (1998).

Luther, E. et al, "Laser Scanning Microscopy Applied to Studies of the Cell Cycle," *Proceedings, Microscopy and Microanalysis*, Bailey, G.W. et al. (eds), Springer, 235–236 (1997).

Mittnacht, S., "Control of pRb Phosphorylation," *Current Opinion in Genetics and Development*, 8:21–27 (1998).

Mittnacht, S. et al., "G1/S Phosphorylation of the Retinoblastoma Protein Is Associated with an Altered Affinity for the Nuclear Compartment," *Cell*, 65(3):381–393 (1991).

Picker, L.J., "Direct Demonstration of Cytokine Synthesis Heterogeneity Among Human Memory/Effector T Cells by Flow Cytometry," *Blood*, 86(4):1408–1419 (1995).

Suni, M.A. et al., "Detection of Antigen–Specific T Cell Cytokine Expression in Whole Blood by Flow Cytometry," *J. Immunol. Methods*, 212:89–98 (1998).

Terada, N. et al., "Differential Regulation of the Tumor Supressor Molecules, Retinoblastoma Susceptibility Gene Product (Rb) and p53, during Cell Cycle Progression of Normal Human T Cells," *J. Immunol.*, 147(2):698–704 (1991).

Waldrop, S.L. et al., "Determination of Antigen–specific Memory/Effector CD4+ T Cell Frequencies by Flow Cytometry," *J. Clin. Inves.*, 99(7):1739–1750 (1997).

Wang, N.P. et al., "Tumor Suppressor Activity of RB and p53 Genes in Human Breast Carcinoma Cells," *Oncogene*, 8:279–288 (1993).

Zarkowska, T. et al., "Monoclonal Antibodies Specific for Underphosphorylated Retinoblastoma Protein Identify a Cell Cycle Regulated Phosphorylation Site Targeted by CDKs," *Oncogene*, 14:249–254 (1997).

Daniel Hochhauser et al., "Effect of Cyclin D1 Overexpression on Drug Sensitivity in a Human Fibrosarcoma Cell Line", *Journal of the National Cancer Institute*, vol. 88, No. 18, pp. 1269–1275 (Sep. 18, 1996).

Michael R. Loken et al., "Coordinate Glycosylation and Cell Surface Expression of Glycophorin A During Normal Human Erythropoiesis", *BLOOD*, vol. 70, No. 6, pp. 1959–1961 (Dec. 1987).

J. Q. Trojanowski et al., "Phosphate–Dependent and Independent Neurofilament Protein Epitopes Are Expressed Throughout the Cell Cycle in Human Medulloblastoma (D283 MED) Cells", *American Journal of Pathology*, vol. 135, No. 3, pp. 747–758 (1989).

* cited by examiner

FLOW CYTOMETRIC METHODS FOR THE CONCURRENT DETECTION OF DISCRETE FUNCTIONAL CONFORMATIONS OF PRB IN SINGLE CELLS

CROSS REFERENCE TO RELATED APPLICATIONS

This application claims priority to U.S. provisional application No. 60/075,908, filed Feb. 25, 1998, the disclosure of which is incorporated herein by reference.

STATEMENT REGARDING FEDERALLY SPONSORED RESEARCH

This work was supported in part by Grant CA R01 28704 from the National Cancer Institute, National; Institutes of Health. The government has certain rights in this invention.

FIELD OF THE INVENTION

The present invention relates to methods, reagents, and reagent kits for detecting discrete functional conformations of proteins concurrently in individual cells, particularly by flow cytometry. In particular, the invention relates to methods, reagents, and reagent kits for the determination of the phosphorylation status of the retinoblastoma susceptibility gene protein (pRB) in individual cells using multiparameter flow cytometry.

BACKGROUND OF THE INVENTION

The recent revolution in genomics technology, and in particular, the development of high density nucleic acid microarrays, has focused extraordinary attention on the differential expression of genes as markers of cellular differentiation, prognosticators of disease, and potential targets for interventional therapy. Brown et al., *Nature Genet.* 21 (Suppl.):33–37 (1999); Duggan et al., *Nature Genet.* 21 (Suppl.):10–14 (1999); Cole et al., *Nature Genet.* 21 (Suppl.):38–41 (1999); Debouck et al., *Nature Genet.* 21 (Suppl.):48–50 (1999). Although an understanding of the cell's transcriptional program is indeed important to all of these goals, the function of many critical proteins is regulated, at least in part, at the posttranslational level, a level to which transcription-based approaches are perforce indifferent.

One such critical protein is that encoded by the retinoblastoma susceptibility gene (pRB; pRb), which plays a pivotal role in the regulation of the cell cycle. pRB restrains cell cycle progression by maintaining a checkpoint in late $G_1$ that controls commitment of cells to enter S phase. The critical role that pRB plays in cell cycle regulation explains its status as archetypal tumor suppressor: loss of pRB function results in an inability to maintain control of the $G_1$ checkpoint; unchecked progression through the cell cycle is, in turn, a hallmark of neoplasia.

pRB activity is controlled by changes in phosphorylation. pRB is hypophosphorylated in normal quiescent cells (in $G_0$ phase) and in cells that are in early $G_1$. With continued progression through $G_1$, cyclin-dependent kinases. (Cdk; Cdk), in association with their respective cyclins, phosphorylate pRB at a number of serine and threonine residues. Unphosphorylated, pRB binds to and sequesters transcription factors of the E2F family. Phosphorylated, pRB discharges these factors, the factors in turn activating transcription of genes coding for proteins regulating DNA replication and cell proliferation. These events commit the cell to entry into S phase. Later, in late mitosis, type 1 protein phosphatases dephosphorylate pRB, restoring the active, E2F-sequestering form, thus resetting the cycle.

pRB is also essential in the terminal differentiation of cells of various lineages. During terminal differentiation, when cells exit the cycle, pRB expression is upregulated and the protein remains in the active—that is, hypophosphorylated—state. Mice homozygously deleted for the RB gene show defective differentiation of various tissues.

Given the critical role that pRB phosphorylation plays in controlling progression of cells through the cell cycle and in mediating terminal differentiation, there exists a need for assays that permit the ready determination of pRB phosphorylation status.

Typically, the phosphorylation status of pRB is assayed in vitro, measuring $^{32}P$-labeling and/or electrophoretic mobility of the protein after isolation and identification by Western blotting. The procedure is cumbersome, and more importantly risks artifactual activation of phosphatases that may dephosphorylate the protein during or after cell lysis. There thus exists a need for methods of measuring pRB phosphorylation in intact cells.

Furthermore, the existing methods measure phosphorylation of pRB in bulk culture. Several questions regarding the mechanism by which pRB controls cell cycle progression cannot be answered using such assays. For example, is phosphorylation of pRB within the cell an all-or-none phenomenon, or is there instead a mixture of hypophosphorylated and hyperphosphorylated pRB molecules at varying proportions throughout the cycle? What proportion of pRB molecules is phosphorylated within the cell during $G_1$, prior to entrance to S phase? Is there a critical threshold in the ratio of hypophosphorylated to hyperphosphorylated pRB molecules that determines the transition of cells to quiescence or to commitment to enter S? Is it the ratio of hypo- to hyperphosphorylated pRB or, rather, the total level of the latter that is critical for cell commitment to enter S phase?

Study of the average behavior of cells in bulk culture also precludes evaluation of heterogeneity in the cycling of individual cells in the population. Such heterogeneity in cell cycle kinetics in tumor cell populations is recognized as a major impediment to successful therapy of cancer. There thus exists a need for methods that permit the heterogeneity of cell cycle kinetics to be assayed, and a particular need for methods that would permit cell cycle heterogeneity to be assessed in populations of tumor cells.

The heterogeneity in the cycling kinetics and timing of cells in culture typically obligates artificial synchronization of the cells in culture to permit meaningful results to be obtained using the existing bulk assays; and yet this cell cycle synchronization, when induced by inhibitors of DNA polymerase, is associated with growth imbalance and unscheduled expression of cyclins. Gong et al., *Cell Growth Differ.* 6:1485–1493 (1995). There thus exists a need for methods that permit the phosphorylation status of pRB to be measured in individual cells without exogenous intervention in the cell cycle.

Methods permitting the phosphorylation status of pRB to be measured in individual cells would prove useful additionally in identifying and characterizing antiproliferative agents that act by halting progression through the cell cycle.

ONCONASE®, initially named protein P30, is a basic protein of 12,000 MW isolated from oocytes or early embryos of *Rana pipiens*. ONCONASE® shows antiproliferative activity in vitro, suppressing proliferation of tumor cell lines of various lineages, including those of hematological origin. ONCONASE® has also been shown to inhibit growth of certain tumors in vivo in mice.

Although ONCONASE® is currently in clinical trials for treatment of patients with advanced pancreatic adenocarcinoma and malignant mesothelioma, the mechanism of its antitumor activity is still poorly understood. The protein is known to have both cytostatic and cytotoxic effects, the former manifesting as an increase in the proportion of cells in $G_1$ phase of the cell cycle; but the mechanism by which the drug effects such cell cycle arrest is unknown. It would be advantageous to have an assay that would permit such a drug's effects on the cell cycle, and in particular, its effect, if any, on pRB phosphorylation, readily to be assayed on a single-cell basis.

Reliable measures of pRB phosphorylation status in individual cells would permit pRB to serve as a marker for distinguishing quiescent from cycling cells. Although certain cell features, such as cellular RNA content, nucleolar mass, chromatin structure (degree of chromatin condensation), expression of the Ki-67 antigen, or expression other proliferation-associated proteins have been proposed as markers distinguishing cycling from noncycling cells, there is as yet no generally accepted, easily measurable marker which discriminates $G_0$ from $G_1$ cells. There thus exists a need in the art for a marker that reliably discriminates quiescent cells from cycling cells.

Recently, two mAbs recognizing human pRB have been described, one of which specifically detects the underphosphorylated form of this protein ($pRB^{P-}$), the other of which reacts with total pRB, regardless of phosphorylation state ($pRB^T$). Dunaief et al., *Cell* 79:119–130 (1994); Wang et al., *Oncogene* 8:279–288 (1993); Terada et al., *J. Immunol.* 147:698–704 (1991); Zarkowska et al., *Oncogene* 14:249–266 (1997). These antibodies have been used to study several aspects of pRB metabolism in bulk culture. There exists a need to adapt these antibodies to methods permitting detection of pRB phosphorylation states in intact cells on a single-cell basis.

SUMMARY OF THE INVENTION

The present invention solves these and other problems in the art by presenting methods and reagents that permit the concurrent and discriminable detection of discrete functional conformations of proteins within a single cell. In particular, the invention provides methods and reagents for the flow cytometric determination of multiple pRB phosphorylation states in individual cells.

We have demonstrated, for the first time, that anti-pRB antibodies that distinguish the phosphorylation state of pRB may successfully be conjugated to fluorophores (fluorochromes) without loss of specificity; that when conjugated to such fluorophores, these antibodies provide sufficient signal to permit detection of pRB in individual cells; that when simultaneously applied to cells that have been fixed and permeabilized, these antibodies bind to their respective functional conformations of pRB within the cell without mutual interference; and that when conjugated to flow cytometrically distinguishable fluorophores, these antibodies permit the concurrent detection of discrete functional conformations (phosphorylation states) of pRB to be detected in single cells.

Using these fluorophore-conjugated antibodies with dyes that bind stoichiometrically to DNA, we have found that the phosphorylation status of pRB may now be correlated with the cell's position in the cell cycle, without the need for artificial synchronization of the cycle. When further used with antibodies specific for other protein components of the cell cycle machinery—such as cyclins, cyclin dependent kinases, and Cdk inhibitors—the methods permit complex intracellular interactions of pRB to be assessed.

Thus, in a first aspect, the present invention provides a method for determining the relative intracellular conformational states of a protein, comprising: contacting a cell with a first antibody, said first antibody specific for a first conformation of said protein, and a second antibody, said second antibody specific for at least one other conformation of said protein, said first and second antibodies being distinguishably labeled; detecting the binding of each of said antibodies concurrently by said cell; and determining the relative binding thereof.

Where the conformational state of the cell may change rapidly, the method may further comprise the antecedent step of fixing the cell. Where the protein is internal to the cell—either cytoplasmic or nuclear—the method further comprises the step, before flow cytometric detection, of permeabilizing the cell.

In preferred embodiments, the antibodies are labeled with fluorophores and the fluorophores are distinguishable by a laser cytometer. Where the laser cytometer is a flow cytometer, the fluorophores are flow cytometrically distinguishable. The fluorophores may conjugated directly or indirectly to the antibodies, with the direct conjugation of at least one, preferably at least two, antibodies presently preferred. Although any fluorophore that permits laser cytometric detection may usefully be employed, those presently preferred are selected from the group consisting of: FITC, PE, PerCP, APC, PE-CY5 tandem fluorophore and PerCP-CY5.5 tandem fluorophore.

In another aspect, the present invention provides a method for determining the relative intracellular conformational states of pRB, comprising: contacting a cell with a first antibody, said first antibody specific for a first conformation of pRB, and a second antibody, said second antibody specific for at least one other conformation of pRB, said first and second antibodies being distinguishably labeled;

1. A method for determining the relative intracellular conformational states of a protein, comprising:
    contacting a cell with a first antibody, said first antibody specific for a first conformation of said protein, and a second antibody, said second antibody specific for at least one other conformation of said protein, said first and second antibodies being distinguishably labeled; detecting the binding of each of said antibodies concurrently by said cell; and then determining the relative binding thereof.

In preferred embodiments of this aspect of the invention, each of the pRB conformations is correlated with a discrete phosphorylation state of the protein. In one such embodiment, the first antibody is specific for a conformation assumed by the hypophosphorylated form of pRB, and the second antibody is specific for at least one other conformation of pRB; this may include specificity for all functional conformations of pRB. In another embodiment, the first antibody is specific for all conformations of pRB, and the second antibody is specific for a subset thereof.

The methods of this second aspect of the invention may further comprise the step of contacting said cell with a fluorescent nucleic acid stain, and then detecting, preferably by laser cytometry, most preferably by flow cytometry, the binding to DNA of said stain concurrently with detecting the binding to pRB of said first and second antibody.

The methods of this aspect may further comprise contacting said cell with a third antibody, said third antibody being specific for a second protein and distinguishable from each of said first and second antibodies, and then detecting the concurrent binding of each of said antibodies to said cell. In preferred embodiments, the second protein may be a cyclin, a cyclin dependent kinase, or a cyclin dependent kinase inhibitor.

In another aspect, the invention provides methods of assaying, or screening, compounds for antiproliferative activity, comprising: contacting a sample of proliferating cells with said compound in vitro; contacting said cells with a first antibody specific for a conformation assumed by the hypophosphorylated form of pRB and a second antibody, said second antibody specific for at least one other conformation of pRB and being flow cytometrically distinguishable from said first antibody; flow cytometrically detecting the binding of each of said antibodies concurrently by said cell; wherein an increased ratio of hypophosphorylated pRB to total pRB indicates antiproliferative activity of said compound.

In a further aspect, the invention provides methods of assessing the in vivo antiproliferative effect of a compound, comprising: contacting a sample of cells obtained from a subject—after the in vivo administration of said compound to said subject—with a first antibody, said first antibody specific for a conformation assumed by the hypophosphorylated form of pRB and a second antibody, said second antibody specific for at least one other conformation of pRB and flow cytometrically distinguishable from said first antibody; and flow cytometrically detecting the binding of each of said antibodies concurrently by said cell; wherein an increased ratio of hypophosphorylated pRB to total pRB, as compared to the ratio obtained from cells identically assayed that were obtained prior to administration of said agent, indicative of in vivo antiproliferative effect.

In yet a further aspect, the invention also provides methods of assessing the proliferative potential of a heterogeneous population of cells, comprising: contacting said cells with a first antibody specific for a conformation assumed by the hypophosphorylated form of pRB and a second antibody, said second antibody specific for at least one other conformation of pRB and flow cytometrically distinguishable from said first antibody; and then flow cytometrically detecting the binding of each of said antibodies concurrently by said cell; wherein cells with a decreased ratio of hypophosphorylated pRB to total pRB are determined to have increased proliferative potential.

In another aspect, the invention provides reagent kits that facilitate the practice of the subject methods. Thus, in one embodiment, the invention provides a kit for detecting the phosphorylation status of pRB in individual cells, comprising: a first antibody, said first antibody specific for a first phosphorylation state of pRB; and a second antibody, said second antibody specific for at least one other phosphorylation state of pRB; wherein said first and second antibodies are flow cytometrically distinguishable from one another. In preferred embodiments, the first antibody is specific for the hypophosphorylated form of pRB and the second antibody is specific for total pRB. In embodiments particularly suited to flow cytometric analysis, each of said antibodies is conjugated to a fluorophore, and said fluorophores are flow cytometrically distinguishable from one another.

BRIEF DESCRIPTION OF THE DRAWINGS

The above and other objects and advantages of the present invention will be apparent upon consideration of the following detailed description taken in conjunction with the accompanying drawings, in which.

DETAILED DESCRIPTION OF THE INVENTION

Figure 1:
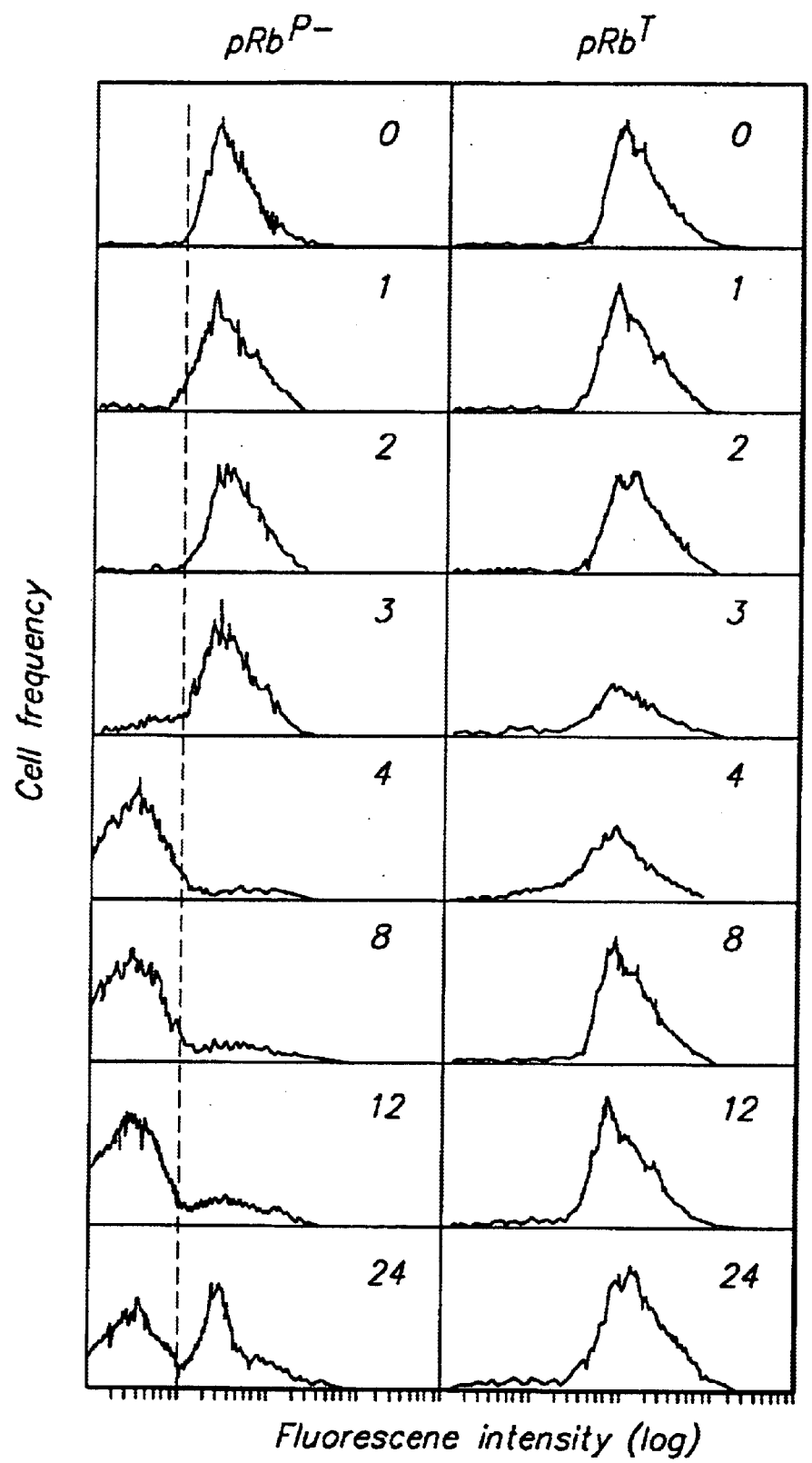
FIG. 1 presents frequency distribution histograms representing the intensity of fluorescence of stimulated lymphocytes reacting with $pRB^{P-}$ mAb (left panels) or $pRB^T$ mAbs (right panels) at different times (0 to 24 hours) after administration of PHA. The dashed lines represent the maximal level of background fluorescence (i.e., the maximal level of fluorescence measured from cells incubated with isotype-matched control IgG1 antibody). Fluorescence intensity is plotted on a three-log exponential scale. The results are representative of three repetitions of the experiments, each providing essentially identical results.

Post-translational modification of proteins, with attendant change in the protein's conformation, is critical to the proper function and regulation of a variety of multicomponent pathways within the cell, ranging from pathways that mediate signal transduction, to anabolic and catabolic pathways, to the pathways that lead to programmed cell death. Such conformational regulation of protein activity is of particular significance in the regulation of the cell cycle, where the reversible, cyclic phosphorylation and dephosphorylation of pRB controls entry of cells into S phase.

Present methods do not readily lend themselves, however, to the concurrent detection of discrete functional conformations of proteins in a single cell. The deficit is particularly notable in methods used to study pRB phosphorylation.

Thus, the phosphorylation status of pRB is typically measured by assessing $^{32}P$-labeling and/or electrophoretic mobility on a Western blot. Not only is the procedure cumbersome, but it also risks the artifactual activation of phosphatases that may dephosphorylate the protein during or after cell lysis, confounding results.

Furthermore, the existing methods for assessing the status of pRB phosphorylation rely upon measurements made in bulk culture. Since the phosphorylation state of pRB changes through the cell cycle, synchronization of the cells in the culture is a prerequisite to such bulk measurements. But such synchronization itself precludes study of the heterogeneity in cell cycle kinetics within the cell population, a subject of intense interest in studies of cancer therapy.

Most antineoplastic therapies derive their selectivity for cancerous cells over normal tissues by targeting the increased proliferative kinetics of tumor cells, relying for specificity upon the tumor cell's increased requirement for nucleic acid synthesis, for cell division, for delivery of nutrition or of oxygen, for removal of waste. Accordingly, it is now well understood that the kinetic heterogeneity of neoplastic cells in a tumor often contributes to therapeutic failure. Present methods preclude meaningful study of individual cells that escape, or that may be predicted to escape, antiproliferative (including antineoplastic) therapy.

Conversely, the identification of chemical agents that directly affect the cell cycle—and in particular, the identification of compounds that can be used to arrest the cell cycle—is made more difficult by the kinetic heterogeneity of bulk cultures. And yet synchronization of such cultures may interfere with or obscure effects that would otherwise be observed using unbiased cells.

To study the relative conformational states of a protein in single cell requires one or more reagents that reliably distinguish between the conformational states of a given protein. The enzymes, suitably engineered substrates may permit discrete functional forms of the protein to be destinguished. For proteins lacking enzymatic activity, however, or for those enzymes for which suitable reporter substrates cannot readily be engineered, antibodies present one of the few realistic approaches.

Among the epitopes to which antibodies bind, some are known to be contributed by the three dimensional conformation of the immunizing protein. It is well known, for example, that antibodies that may be well identify denatured proteins of western blot may monetheless prove incapable of recognizing protein in its native conformation; similarly, antibodies are known that permit immunocytochemical or immunofluorescence detection of proteins in formalin-fixed, paraffin-embedded tissue sections but that cannot recognize native protein. While it is not uncommon to find antibodies that discriminate native from denatured forms of a protein, however, it is far less common to find antibodies that recognize two different functional conformations of a protein.

Recently, two mouse mAbs that recognize different conformational states of the human RB protein have been described. One of these antibodies (clone G99-549) specifically detects the underphosphorylated (hypophosphorylated) form of the protein (pRB$^{P-}$); the other (clone G3-245) reacts with total pRb regardless of phosphorylation state (pRB$^T$). Dunaief et al., *cell* 79:119–130 (1994); Wang et al., *Oncogene* 8:179–288 (1993); Terada et al., *J. Immunol.* 147:698–704 (1991); Zarkowska et al., *Oncogene* 14:249–266 (1997). Both are now commercially available (PharMingen, San Diego, Calif.).

Hybridoma clone G99-549 was derived originally from a fusion in which underphosphorylated human pRB, produced in sf9 insect cells, was used as immunogen. Of the hybridoma clones that produced antibody that recognized pRB in Western blots, only a single clone, G99-549, produced antibody that identified the faster-migrating, and presumably underphosphorylated, forms of pRB. Several control experiments have since demonstrated that the faster migrating forms of pRB recognized by this mAb on Western blot indeed lack phosphorylation.

The epitope recognized by G99-549 (anti-pRB$^{P-}$; pRB$^{P-}$ mAb) lies between pRB amino acids 514–610, within an "A box" of a T-antigen binding pocket domain of human pRB. The location of this epitope suggests that G99-549 mAb recognizes a structural conformation that pRB assumes in the hypophosphorylated state, rather than directly recognizing the unphosphorylated form of a phosphorylation consensus sequence. In contrast, clone G3-245 (anti-pRB$^T$; pRB$^T$ mAb; also termed Mh-RB-02) appears to recognize pRB in all of its functional conformations, recognizing an epitope mapping to between amino acids 300 and 380 of human pRB.

To use such conformation-specific antibodies for flow cytometric detection, however, a number of technical problems must first be solved.

First, conjugation to fluorophore (either directly, or indirectly) is required; yet not all antibodies can successfully be conjugated to fluorophore with retention of antigen specificity.

Second, once conjugated, the antibodies must provide sufficient signal to permit detection in individual cells.

Several groups have recently described multiparametric flow cytometry assays that permit detection of intracellular proteins at the single cell level. Picker et al., *Blood* 86(4):1408–1419 (1995); Waldrop et al., *J. Clin. Invest.* 99:1739–1750 (1997); Ghanekar et al., *J. Immunol.* 157:4028–4036 (1996); de Saint-Vis et al., *J. Immunol.* 160:1666–1676 (1998); Suni et al., *J. Immunol.* 212:89–98 (1998). For the most part, however, these assays have been directed to detection of proteins that are normally secreted from the cell; incubation of these cells with a secretory inhibitor permits the signal to be amplified before assay through accumulation of protein in the cytoplasm. The assays have not been directed to detection of unamplified nuclear proteins.

Third, in order to detect multiple functional conformations of a protein concurrently in a cell, the reagents that distinguish these conformations must not interfere with or abrogate the binding of one another. Where the conformations are mutually exclusive, this requirement is easily met, since the antibodies must bind to separate molecules; where one antibody recognizes a subset of the conformations recognized by the other, however, the antibodies must both bind to a single molecule in one or another conformation, implicating steric hindrance as a potential problem.

Finally, for concurrent detection of discrete functional conformations of a single protein in a single cell, each antibody must permit conjugation to a fluorophore, the two fluorophores being flow cytometrically distinguishable, without loss of specificity and without fluorescence quenching.

Successful development of a suitable assay for single cell detection of multiple conformational states of a protein requires that each of these conditions be satisfied, and yet there is no ready way a priori to predict whether any given antibodies will be able to satisfy these rigorous requirements.

We have now succeeded in conjugating anti-pRB antibodies that distinguish discrete phosphorylation states of pRB to fluorophores (flubrochromes) without loss of specificity. We have found that when conjugated to such fluorophores, these antibodies provide sufficient signal to permit detection of pRB in individual cells; that when simultaneously applied to cells that have been fixed and permeabilized, bind to their respective functional conformations of pRB within the cell without mutual interference; and that when conjugated to flow cytometrically distinguishable fluorophores, permit the concurrent detection of discrete functional conformations (phosphorylation states) of pRB to be detected in single cells. We have, as a result, been able to develop a flow cytometric assay that permits detection of discrete pRB phosphorylation states in individual cells.

As described in detail in the Examples below, the flow cytometric methods of the present invention have been applied to normal peripheral blood lymphocytes after stimulation with polyclonal mitogen (Example 1), to the human promyelocytic leukemic cell line HL-60 (Example 2), and to human histiocytic U937 cells (Example 3). In outline, the procedure is similar for each of these cell types.

Briefly, cells are fixed, labeled with antibodies conjugated to flow cytometrically detectable fluorophores (fluorochromes), and then detected using single- or dual-laser multiparametric flow cytometry.

Flow cytometric techniques are by now well established. Detailed protocols are compiled in several recent compendia, including *Flow Cytometry: A Practical Anproach*, 2nd ed., M. G. Ormerod (ed.), Oxford University Press (1997); *Handbook of Flow Cytometry Methods*, J. Paul Robinson (ed.), John Wiley & Sons (1993); *Current Protocols in Cytometry*, J. Paul Robinson (ed.), John Wiley & Sons (October 1997, with periodic updates); *Becton Dickinson Cytometry Source Book*, Becton Dickinson Immunocytometry Systems (1998, with periodic updates)(San Jose, Calif.), the disclosures of which are herein incorporated by reference.

The first step in the flow cytometric detection of pRB functional conformations is fixation of the cells; fixation both arrests metabolic processes and, simultaneously, renders the cytoplasm and nucleus accessible to the labeling antibodies. In the Examples presented hereinbelow, fixation was accomplished either by: (1) suspending in 1% formaldehyde in PBS for 15 min on ice, followed after washing by resuspension in ice-cold 80% ethanol, further followed after rinsing by resuspension in 0.25% Triton X-100 (Sigma); or by (2) fixation in either ice-cold 80% ethanol or absolute methanol for up to 24 h, followed by washing and then suspension in Triton X-100. As would be well known in the art, other fixation protocols and reagents may equally be used.

Cells may, for example, be simultaneously fixed and permeabilized in HBSS (HEPES buffered saline) with 10 mmol/L HEPES buffer, 4% paraformaldehyde, and 0.1% saponin for 10 to 15 minutes at 4° C. Alternatively, cells may be permeabilized using commercially available reagents, such as FACS™ Permeabilization Solution (Becton Dickinson Immunocytometry Systems cat. no. 340457). FACS™ Permeabilizing Solution is designed to overcome the limitations of saponin-based permeabilizing reagents; saponin, a compound derived from plants, is a common source of variability in intracellular immunophenotypic staining because of its heterogeneous composition.

Next, the cells are labeled with antibodies conjugated to flow cytometrically detectable fluorophores (fluorochromes). As is of course well understood, the antibodies may be directly conjugated to fluorophores or may be labeled indirectly, using a fluorophore-conjugated secondary antibody that recognizes the primary antibody. Direct conjugation is preferred when feasible.

In the simplest version of the methods of the present invention, only two antibodies are used—pRB$^{P-}$ mAb and pRB$^T$ mAb—and the antibodies need only be labeled with fluorophores that are mutually distinguishable. As is well known in the art, there are a number of two-fluorophore combinations that permit concurrent and discriminable detection using a single laser; other combinations become available when additional lasers, with different emission spectra, are used for detection.

Fluorophores that may readily be used in the practice of the present invention include FITC (fluorescein isothiocyanate), PE (phycoerythrin), PerCP (peridinium chlorophyll protein), APC (allophycocyanin), PE-CY5 tandem fluorophore (phycoerythrin-cyanine 5 tandem resonance energy transfer fluorophore; CYCHROME®) and PerCP-CY5.5 tandem fluorophore. Other fluorophores known in the art may also be used, as may molecules such as biotin, for which specific binding cognates (such as streptavidin) may then be used to target fluorophore-conjugated secondary antibodies.

For two-color flow cytometry, we have found CYCHROME® and FITC to be a particularly useful combination (anti-pRB$^T$ conjugated to CYCHROME®, and anti-pRB$^{P-}$ mAb conjugated with FITC). However, PE may also be used in combination with FITC, and presents certain advantages in quantitation. PE is particularly well-suited to quantitative analysis: it is bright, and it does not self-quench. Fluorophores such as fluorescein isothiocyanate (FITC), CY3 and CY5 can self-quench due to overlap of their excitation and emission spectra. Quenching of FITC has been shown to occur both through proximity of FITC molecules on a single antibody and through the proximity of FITC molecules on adjacent antibodies directed to a high density cellular epitope. Haugland, *Handbook of Fluorescent Probes and Research Chemicals*, 6th ed., Molecular Probes Inc., Eugene, Oreg. (1996); Deka et al., *Cytometry* 25:271–279 (1996). Peridinium chlorophyll protein (PerCP), (described, inter alia, in U.S. Patent No. 4,876,190, incorporated herein by reference) photolyses during its transit through the laser of the. flow cytometer, precluding accurate quantitation. Other advantages of PE for antigen density quantitation are described in U.S. Pat. No. 5,620, 842, incorporated herein by reference. A further advantage of PE as a fluorophore is the commercial availability of pelletized bead standards QUANTIBRITE™, Becton Dickinson Immunocytometry Systems, San Jose, Calif.) that provide defined levels of PE fluorescence, permitting standard curves to be constructed that then permit the derivation of the number of antibodies bound per cell.

Present multiparametric flow cytometric techniques permit more than two antibodies to be discriminably detected in, a single assay. As additional fluorophores are developed and additional lasers integrated into flow cytometers, it will be possible to use an increasing number of such antibodies in a single assay. In the methods of the present invention, these further antibodies may, for example, be used to report, concurrently with the phosphorylation status of pRB, the concurrent levels of other proteins that participate in the regulation of the cell cycle.

Thus, antibodies may be used that bind to cyclins, including cyclin A, cyclin B1, cyclin C, cyclin D1, cyclin D2, cyclin D3, cyclin E, cyclin F, cyclin G, cyclin H, cyclin I, and cyclin K. Antibodies may also be used that have specificity for cyclin dependent kinases, such as Cdk1, Cdk2, Cdk3, Cdk4, Cdk5, Cdk6, Cdk7 and Cdk8, or for cyclin dependent kinase inhibitors, including p15$^{INK4b}$, p16$^{INK4a}$, p18$^{INK4}$, p19$^{INK4c}$, p21$^{WAP1/CIP1}$, and p27$^{Kip1}$.

Such antibodies are commercially available (PharMingen, San Diego, Calif.; Serotec, Oxford, UK). Detection of a number of these proteins is exemplified hereinbelow.

In addition to the detection of other cell cycle proteins, multiparametric analysis permits the concurrent measurement of DNA content. Measurement of DNA content enables the pRB phosphorylation state to be correlated in each cell with the cell's position in the cell cycle; this, in turn, permits direct analysis of pRB phosphorylation status in asynchronous, exponentially growing cell populations.

In order to correlate pRB expression with cell cycle stage, the DNA content of the cell may simultaneously be determined using a fluorescent nucleic acid stain. Typically, cells are counterstained with 1 μg/ml of 4,6-diamidino-2-phenyl indole (DAPI; Molecular Probes Inc., Eugene, Oreg.) in PBS, or with 5 μg/ml of propidium iodide (PI; Molecular Probes) in PBS with 0.1% RNase (Sigma).

Although DAPI and PI are routinely used for such purposes, other nucleic acid stains may also be used, including both cell-permeant nucleic acid stains and, with concomitant use of fixatives that permeabilize the cell, with cell-impermeant nucleic acid stains as well.

Included among such stains are Hoechst 33258 and Hoechst 33342 which, like DAPI, are blue fluorescent dyes that bind to the minor groove of DNA at AT-rich sequences. Hoechst 33342 more rapidly permeates cells than Hoechst 33258, and is thus commonly used for determining the DNA content of viable cells without detergent treatment or fixation; when cells are fixed and/or permeabilized for flow cytometric detection of other intracellular components (such as pRB and cyclins), Hoechst 33258 also proves useful. Like DAPI, the Hoechst dyes can be excited by a mercury-arc lamp, the UV spectral lines of the argon-ion laser, or the 325 nm spectral line of the He-Cd laser. Also like DAPI, the Hoechst dyes preferentially bind to AT-rich sequences and exhibit higher quantum yields when bound to AT-rich nucleic acids, thus introducing a strong bias into the measurements of nuclear DNA content. As a consequence, data obtained with Hoechst 33342, 33358 and DAPI correlate very well with each other but less well with data obtained with propidium iodide, a red fluorescent, cell-impermeant nucleic acid stain.

Ethidium bromide, ethidium homodimer-1 (Molecular Probes, Inc., Eugene, Oreg., cat. no. E-1169), and hexidium iodide (Molecular Probes cat. no. H-7593), like propidium iodide, are phenanthridinium derivatives that intercalate between the bases of DNA in fixed cells, yielding red fluorescent signal. Unlike DAPI and the Hoechst dyes, these dyes bind DNA stoichiometrically with little or no sequence preference. Because these base-intercalators are not specific for DNA, cell-cycle analysis requires treatment of fixed samples with RNase to eliminate fluorescence resulting from dye binding to RNA.

SYTOX Green nucleic acid stain (cat. no. S-7020, Molecular Probes Inc., Eugene, Oreg.; excitation maximum 504 nm, emission maximum 523 nm) is particularly useful for cell-cycle analysis on RNase-treated fixed cells. SYTOX Green is a high-affinity nucleic acid stain that easily penetrates cells with compromised plasma membranes, such as those that have been permeabilized and/or fixed. SYTOX green produces lower coefficients of variation than, propidium iodide, and unlike DAPI or Hoechst dyes, shows little base selectivity. These properties, combined with is 1000-fold fluorescence enhancement upon nucleic acid binding and its high quantum yield make it an excellent quantitative indicator of DNA content in RNase-treated cells.

Other nucleic acid fluorescent dyes include acridine orange, which emits green fluorescence when bound to double-stranded nucleic acids and red fluorescence when bound to single-stranded nucleic acids. This spectral property has been exploited in methods for simultaneously analyzing the DNA and RNA content of a cell culture. Also useful for measurement of DNA content, and thus determination of cell-cycle status, is 7-aminoactinomycin D (7-AAD, cat. no. A-1310, Molecular Probes, Inc., Eugene, Oreg.). 7-AAD is a fluorescent intercalator that undergoes a spectral shift upon association with DNA; 7-AAD/DNA complexes can be excited by the argon-ion laser and emit beyond 610 nm. This visible light-excitable nucleic acid stain is suitable for cell-cycle analysis, although it exhibits selectivity for binding to GC regions of DNA.

Other alternatives include dimeric cyanine dyes in the TOTO and YOYO series (Molecular Probes, Inc., Eugene, Oreg.), most of which have proven useful in staining nucleic acids in fixed cell preparations.

In addition to staining the nucleic acid of cells after fixation, cells may be grown in media that permits incorporation into DNA of halogenated pyrimidine analogues that may then be detected flow cytometrically. For example, cells may be pulse-labeled with 5-bromodeoxyuridine (5-BrdU), and then subsequently contacted with an anti-5-BrdU antibody. Wilson, "Analysis of DNA-measurement of cell kinetics by the bromodeoxyuridine/anti-bromodeoxyuridine method," in Flow *Cytometry: A Practical Approach* pp. 137–156, Ormerod. (ed.), IRL Press (Oxford, UK) 1994, incorporated herein by reference. Because the fluorescence of bis-benzimidazole dyes bound to DNA is quenched by 5-BrdU, continuous labeling with BrdU and subsequent staining with Hoechst 33258 allows the discrimination of chromatids according to the number of replications undertaken during incubation in BrdU.

In Example 1, below, we demonstrate that two anti-pRB monoclonal antibodies—anti-pRB$^{P-}$ and anti-pRB$^{T}$—are able to recognize and to bind their cognate epitopes simultaneously, a prerequisite to the concurrent measurement of multiple functional conformations of the pRB protein. Example 1 further demonstrates that these antibodies may, after conjugation to flow cytometrically distinguishable fluorophores, be used in multiparameter flow cytometric assays to report the phosphorylation status of pRB in individual cells.

The flow cytometric studies reported in Example 1 reveal, inter alia, that pRB is underphosphorylated in over 98% of unstimulated normal lymphocytes, and that the proportion of cells with underphosphorylated pRB drops to 20% between 3 and 8 hours after addition of the polyclonal mitogen, phytohemagglutinin (PHA). This novel result makes the phosphorylation status of pRB a useful marker of early lymphocyte activation, nicely complementing the use of CD69 in the identification—and gating—of activated T lymphocytes in antigen-specific assays, as described in Picker et al., *Blood* 86 (4):1408–1419 (1995); Waldrop et al., *J. Clin. Invest.* 99:1739–1750 (1997), and Suni et al., *J. Immunol.* 212:89–98 (1998). Example 1 further demonstrates that phosphorylation of pRB within a cell is rapid and complete, since reactivity of individual lymphocytes with anti-pRB$^{P-}$ mAb was lost abruptly, rather than step-wise, during stimulation. The data show that phosphorylation affects nearly all pRB molecules within each individual cell. These data answer questions that could be neither posed nor answered with the prior art bulk techniques.

Because the reactivity with anti-pRB$^{T}$ mAb during lymphocyte stimulation was essentially constant (FIGS. 1 and 2), labeling with anti-pRB$^{P-}$ alone (FIG. 1) gave essentially the same results as measurement of the ratio of pRB$^{P-}$:pRB$^T$ (not shown), and either measure could have been used in these initial experiments. However, the ratiometric analysis of pRB$^{P-}$:pRB$^T$ is essential when the total level of pRB changes, as is seen, e.g., in Example 2, below; without concurrent measurement of pRB$^{P-}$ and pRB$^T$, the degree of pRB phosphorylation cannot reliably be compared. And despite the constancy of total pRB in lymphocytes assayed in Example 1, simultaneous analysis using the combination of anti-pRB$^{P-}$ and anti-pRB$^T$ mAbs made it possible to ascertain with certainty that the observed loss of reactivity with anti-pRB$^{P-}$ indeed reflected changes in the degree of pRB phosphorylation, rather than a decrease in cellular content of this protein. These conclusions could not have been reached with prior methods.

Figure 2:
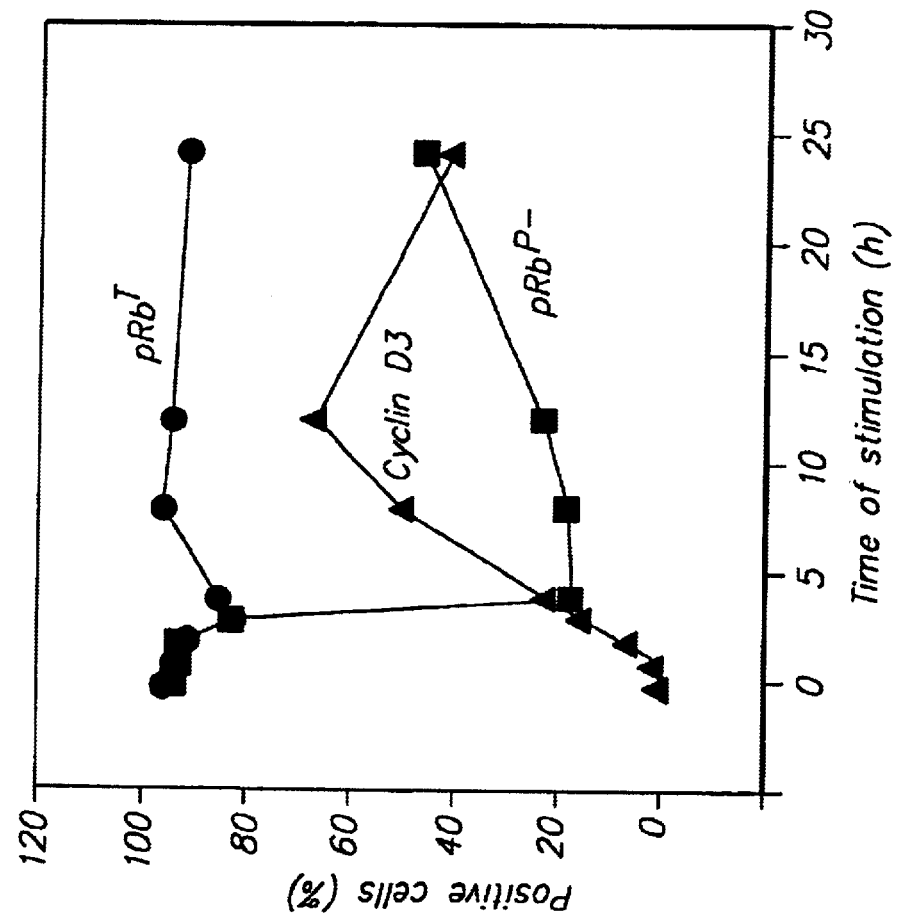
FIG. 2 shows changes in percentage of lymphocytes reacting with anti-$pRB^{P-}$ or anti-$pRB^T$ mAb, as well as the cells expressing cyclin D3, as a function of the duration of incubation with PRA.

During G$_1$ phase, pRB is phosphorylated by Cdk4 and in some cell types, also by Cdk6. In the case of lymphocytes, Cdk4 is activated by cyclins D2 and D3. Adding a third antibody to the multiparametric flow cytometry assay described herein permits pRB phosphorylation to be correlated, on a cell-by-cell basis, with the presence of these other proteins. Thus, experiments reported in Example 1 demonstrate that the initiation of pRB phosphorylation during lymphocyte stimulation, seen 3 hours after addition of mitogen, coincides with the appearance of cells expressing cyclin D3 (FIG. 2).

Further, the flow cytometric assay may be performed using reagents that permit the concurrent measurement of DNA content, allowing pRB status to be correlated with the cell's position in the cell cycle, even in asynchronous, exponentially growing cell populations, without necessity for culture synchronization. Cell synchronization by inhibitors of DNA replication introduces experimental bias due to induction of a severe imbalance of cyclin expression. The present approach, therefore, may be uniquely suitable to assay the status of pRB phosphorylation in individual cells without perturbing their progression through the cycle.

Example 1 further demonstrates the utility of the methods of the present invention in elaborating the mechanism of action of antiproliferative agents. It has been shown previously that staurosporine (STP), a nonspecific protein kinase inhibitor, arrests lymphocytes and fibroblasts early in G$_1$, past the point of induction of cyclins D3 and D2 but prior to induction of cyclin E. Fibroblasts and cells of human lung or breast cancer lines that have been arrested in G1 by STP have underphosphorylated pRB. The possible target of STP in all these cells may be Cdk4, but evidence is mixed: other data suggest that the STP-induced arrest in G$_1$ may be associated with the induction and accumulation of p18 and p27$^{KIP}$ Cdk inhibitors. Experiments reported in Example 1 demonstrate that STP prevents pRB phosphorylation, providing novel approaches to analyzing the agent's action. Example 3 further demonstrates the utility of the present methods for analyzing, and screening for, antiproliferative activity of chemical agents. Because the assay utilizes intact cells rather than cell extracts, the permeability of the studied agents through the plasma membrane may be determined at the same time. Of course, permeability-enhancing adjuncts, such as are known in the art, may be employed to study the effects of otherwise impermeable agents.

Furthermore, because individual cells are analyzed, the methods of the present invention make it possible to estimate the intercellular variability in cell cycle kinetics, and to detect rare cells or cell subpopulations having different properties. This is of particular importance in light of the evidence that heterogeneity of tumor cell populations contributes to therapeutic failure; it would be clinically useful to identify the few cells that survive and are responsible for the relapse.

In the experiments reported in Example 2, below, pRB phosphorylation was further analyzed in HL-60 leukemic cells during proliferation in culture and during induction of differentiation of these cells by various agents.

Expression of pRB and its state of phosphorylation were flow cytometrically assayed in HL-60 cells during their proliferation and after induction of differentiation. Correlated measurements of pRB$^{P-}$, pRB$^T$, pRB$^{P-}$:pRB$^T$, and cellular DNA content revealed that following mitosis (during the exponential phase of cell growth), a mixture of hypo- and hyperphosphorylated pRB was present within the cell for less than 2 hours, i.e., early in G$_1$; no hypophosphorylated pRB was detected throughout remainder of the cycle. Cellular pRB content was also shown to increase, primarily during G$_1$; entrance of the cell into S phase was correlated with reaching a distinct threshold level of pRB. No correlation was seen between the content of pRB per cell and its state of phosphorylation during G$_1$.

Cell differentiation—whether induced by 1,25-dihydroxyvitamin D$_3$, retinoic acid, or phorbol myristate acetate (PMA)—led to cell arrest primarily in G$_{0/1}$. The G$_{0/1}$ cells in these cultures, compared to G$_1$ cells from the untreated cultures, had increased level of both pRB$^T$ and pRB$^{P-}$. However, because the relative increase of pRB$^{P-}$ was disproportionately greater than of pRB$^T$, the pRB$^{P-}$/pRB$^T$ ratio of the differentiating cells was markedly elevated. The cells that still were in S and G$_2$/M in the differentiating cultures also showed the presence of hypophosphorylated pRB.

These data suggest that the mechanism of irreversible cell cycle arrest during terminal differentiation involves both the increase in pRB amount and dephosphorylation of the pRB already present within the cell. This provides a large pool of hypophosphorylated pRB that can effectively sequester all free E2F, thereby precluding activation of the genes whose transcription is needed to pass the G$_1$ restriction point. In contrast to terminal differentiation, transient quiescence (G$_0$ state) manifests only by dephosphorylation of pRB, without a change in its cellular level.

The present data indicate that regardless whether differentiation of HL-60 cells was induced along a myelogenous pathway, as in the presence of RA, or along a monocytic pathway, as by vitamin D3 or PMA, the hypophosphorylated pRB predominated over its hyperphosphorylated form within individual cells. This observation is in agreement with the vast amount of data in the literature that indicates that pRB becomes hypophosphorylated during differentiation of cells of various lineages. Likewise, the observed rise in total pRB per cell as reflected by the increased binding of anti-pRB$^T$ is concordant with the published data showing that expression of this protein increases during cell differentiation regardless of the cell system.

Example 3 further demonstrates that the methods of the present invention may be used to investigate the mechanism of action of antiproliferative (including antineoplastic) agents, and may be used to screen compounds for such effects.

The mechanism of antitumor activity of ONCONASE®, a 12 kDa amphibian protein homologous to pancreatic RNase A, is still poorly understood. The protein shows cytostatic and cytotoxic activity in vitro, inhibits growth of tumors in vivo in mice, and is presently in phase III clinical trials in human patients. In light of the evidence that ONCONASE® suppresses cell proliferation, we applied the novel flow cytometric methods described herein to an analysis of the effects of ONCONASE® on various components of the cell cycle machinery.

Human histiocytic lymphoma U937 cells were treated with ONCONASE® and expression of cyclins D3 and E, as well as of the cyclin-dependent kinase inhibitors (CKIs) $p16^{INK4A}$, $p21^{WAP1/CIP1}$ and $p27^{KIP1}$ (all detected immunocytochemically) was measured by multiparameter flow cytometry, in relation to the cell cycle position. Also monitored was the status of phosphorylation of retinoblastoma protein (pRB).

Cell incubation with 170 nm ONCONASE® for 24 hours and longer led to their arrest in $G_1$, which was accompanied by a decrease in expression of cyclin D3, no change in cyclin E, and enhanced expression of all three CKIs. pRB was underphosphorylated in the ONCONASE®-arrested $G_1$ cells but was phosphorylated in the cells that were still progressing through S and $G_2/M$ in the presence of ONCONASE®. The cytostatic effect of ONCONASE® thus appears to be mediated by downregulation of cyclin D3 combined with upregulation of $p16^{INK4A}$, $p21^{WAF1}$ and $p27^{KIP1}$, the events which may prevent phosphorylation of pRB during $G_{0/1}$, and result in cell arrest at the restriction point controlled by Cdk4/6 and D type cyclins.

The Examples summarized above and presented in detail below demonstrate that the flow cytometric methods of the present invention may be applied to a wide variety of suspension cell types, from normal lymphocytes, to HL-60 leukemic cells, to human histiocytic lymphoma U937 cells. Such flow cytometric methods may also be applied to any adherent cell type that permits of dispersal, before or after fixation, as a unicellular suspension in fluid media.

Recently, the development of the laser scanning cytometer (LSC®, CompuCyte, Cambridge, Mass.) has expanded the boundaries of fluorescence-based cytometry to include analysis of cells that are embedded within solid tissue sections disposed upon glass slides. Such laser scanning cytometers have proven particularly useful in fluorescence-based cytometric assays of cell cycle events. Juan et al., Methods Mol Biol., 91: 67–75 (1996); Juan et al., Cell Biol. 2: 261–273 (1998); Juan et al., Cell Biol. 2: 341–350 (1998); Clatch et al., Cytometry 34: 36–38 (1998); Luther et al., Microscopy & Microanalysis, 3: 235–236 (1997). The present reagents and methods may readily be adapted for detection by LSC® devices.

Furthermore, the methods of the present invention are not limited to fluorescence-based detectors. The antibodies of the present invention may equally be conjugated, directly or indirectly, to moieties that generate light-absorptive reporters. For example, the enzymes may be conjugated, directly or indirectly, to enzymes such as alkaline phosphatase that generate dyes, the light absorption of which may be detected using colorimeters, including appropriately-filtered scanning confocal microscopes. By whatever method detected, however, the antibodies must be mutually distinguishable.

Whichever device is used for detection, the methods of the present invention may be applied to surveys of the cell cycle status of primary tumor cells. Given the cell cycle dependence of standard antineoplastic therapies, the methods of the present invention find use both in advance of, and following, therapy. Before treatment, survey of the cell cycle kinetics of a tumor sample, acquired by biopsy, excision, or venipuncture, will provide an indication of the percentage of cells that may be targeted by such therapy. After treatment, a similar assessment may identify cells that have escaped treatment but that retain abnormal proliferative potential. Proliferative states short of neoplasia, such as those found, e.g., in psoriasis, adenomas, benign prostatic hypertrophy, uterine fibroids, and the like, may similarly be analyzed.

The present methods are thus particularly useful in clinical settings and will thus likely be performed, inter alia, by clinical laboratories. Flow cytometry has now become a routine part of the clinical laboratory, Riley et al., *Clinical Aoplications of Flow Cytometry*, Igaku-Shoin Medical Publ. (1993); Coon et al. (eds.), *Diagnostic Flow Cytometry* (Techniques in Diagnostic Pathology, No 2), Williams & Wilkins (1991); Keren et al., *Flow Cytometry and Clinical Diagnosis*, Amer. Soc'y of Clinical Pathol. (ISBN 0891893466, 1994), and the methods presented herein are well within the skill of the clinical pathologist.

However, any one clinical laboratory may have only sporadic need to perform the assay, and there is thus a need for compositions and kits that permit the assay readily to be performed on an as-needed basis. Thus, in another aspect, the present invention provides reagents and kits that permit the assay readily to be performed on an as-needed basis. A typical embodiment of such a kit includes two antibodies, discriminably labeled, each of which recognizes a different functional conformation of the pRB protein. In preferred embodiments, one antibody recognizes the hypophosphorylated form of human pRB, and the other recognizes total pRB.

Although the Examples focus particularly on correlating pRB phosphorylation status with that of other components of the cell cycle machinery—cyclins, cyclin dependent kinases, and cyclin-dependent kinase inhibitors—the multiparameter nature of the flow cytometric methods described here permit concurrent measurement of pRB functional conformations with other proteins. For example, the molecular events that attend antigen-specific lymphocyte activation are of tremendous interest in both basic and clinical immunology. Picker et al., *Blood* 86 (4):1408–1419 (1995); Waldrop et al., *J. Clin. Invest.* 99:1739–1750 (1997); Suni et al., *J. Immunol.* 212:89–98 (1998). The present methods readily permit pRB phosphorylation to be assessed concurrently with cytokine production, CD69 expression, and the like.

As noted above, the $pRB^{P-}$ mAb appears to bind a conformational epitope in the SV40 large T binding region on pRB. Abrogation of the binding of the antibody may thus usefully permit screening of antibodies or anti-tumor drugs that target those processes that are altered by tumor antigens.

The $pRB^{P-}$ may, of course, also be used to monitor, direct, and effect purification of the hypophosphorylated form of pRB. The antibody's antigen-binding domain may further be used as a model for drug screening, evaluation, or design; as a model for an inhibitor of Rb; and as an agent directly useful in gene therapy.

Certain aspects of the present invention are, described in Juan et al., *J. Exp. Cell Res.* 239:104–110 (1998); Juan et al., *Exp. Cell Res.* 244:83–92 (1998); Juan et al., *Clinical Immunol. Newsletter 18* (9):89–94 (1998); Juan et al., *Leukemia* 12:1241–1248 (1998), the disclosures of which are incorporated herein by reference, and in the following illustrative and nonlimiting examples.

EXAMPLES

In general, and unless otherwise stated, the flow cytometric methods used in the following examples are well known in the art. Detailed protocols are compiled in several recent compendia, including *Flow Cytometry: A Practical Approach*, 2nd ed., M. G. Ormerod (ed.), Oxford University Press, 1997; *Handbook' of Flow Cytometry Methods*, J. Paul Robinson (ed.), John Wiley & Sons (1993); *Current Protocols in Cytometry*, J. Paul Robinson (ed.), John Wiley & Sons (October 1997, with periodic updates); *Becton Dickinson Cytometry Source Book*, Becton Dickinson Immunocytometry Systems (1998, with periodic updates)(San Jose, Calif.), the disclosures of which are herein incorporated by reference.

Fluorophore abbreviations are as follows: phycoerythrin (PE), peridinium chlorophyll protein (PerCP), allophycocyanin (APC), fluorescein isothiocyanate (FITC), cyanine 5 (CY5), cyanine 5.5 (CY5.5), CYCHROME® (PE/CY5 tandem fluorophore); and PerCP/CY5.5 (PerCP/CY5.5 tandem fluorophore)

Example 1

Flow Cytometric Measurement of pRB Protein Phosphorylation in Mitogen-Stimulated Lymphocytes Cells, Drugs Human peripheral blood lymphocytes, obtained from healthy volunteers by venipuncture, were isolated by density gradient centrifugation. The cells were washed twice with phosphate-buffered saline (PBS), resuspended in RPMI 1640 medium supplemented with 10% fetal calf serum, 100 units/ml penicillin, 100 µg/ml streptomycin and 2 mm L-glutamine at a density of $10^6$ cells/ml, treated with 10µg/ml of phytohemagglutinin (PHA) and incubated at 37.5° C. in the mixture of 95% air and 5% $CO_2$ for the periods of time shown in the respective figure legends. The medium, supplements, and antibiotics were obtained from Life Technologies (Grand Island, N.Y.), PHA from Sigma Chemical Co. (St. Louis, Mo.).

Stock solution of staurosporine (STP; Kamiya Biomedical Co., Thousand Oaks, Calif.) was made in dimethyl sulfoxide (DMSO) at a concentration 0.2 mM and was stored at −20° C. (Juan et al., *Exp. Cell Res.* 227:197–202 (1996). Staurosporine, an alkaloid (NW 466 Dalton) isolated from the culture broth of *Streptomyces staurospores* is a nonspecific protein kinase inhibitor. This reagent was used in cultures at a final concentration of 20 nM, which arrests lymphocytes in G1 but does not interfere with the induction of cyclin D3 (see Juan et al., *Exp. Cell Res.* 227:197–202 (1996)).

Immunocytochemical Detection of $pRB^T$ and $pRB^{P-}$

The cells were washed with PBS and fixed in suspension in 1% formaldehyde in PBS for 15 min on ice. The cells were then washed with PBS and resuspended in ice-cold 80% ethanol for up to 24 h. After fixation the cells were rinsed twice with PBS and resuspended in 100 µl of PBS containing 0.25% Triton X-100 (Sigma), 1% bovine serum albumin (BSA; Sigma) and 1.2µg/ml of the anti-$pRB^T$ mAb (clone G3-245; PharMingen cat. no. 14001A) conjugated with CYCHROME® and/or with 1 µg/ml of anti-$pRB^{P-}$ mAb (clone G99-549; PharMingen cat. no. 14441A), conjugated with FITC and incubated for 2 hours at room temperature. The cells were then rinsed with PBS containing 1% BSA and their fluorescence was measured by flow cytometry.

In some experiments in addition to the detection of pRB, the cells were counterstained with 1 µg/ml of 4,6-diamidino-2-phenyl indole (DAPI; Molecular Probes Inc., Eugene, Oreg.) in PBS, or with 5 µg/ml of propidium iodide (PI; Molecular Probes) in PBS with 0.1% RNase (Sigma) for multivariate analysis of pRB and DNA.

To demonstrate specificity of the mAbs with respect to pRB phosphorylation, the cells in control experiments were preincubated with 4 units of alkaline phosphatase (type VII from bovine intestinal mucosa; Sigma) in 100 µl of Tris buffer (Sigma) at pH 9.4 for 30 min before incubation with mAbs. Other controls consisted fluorochrome-conjugated isotype-matched mAb with specificity for irrelevant antigen (IgG1; clone MOPC-21, PharMingen cat. no. 03171D).

Immunocytochemical Detection of Cyclin D3

After cell fixation (as described above) the cells were washed twice with PBS, suspended in 1 ml of 0.25% Triton X-100 in PBS, kept on ice for 5 min, centrifuged (300 g; 5 min) and the cell pellet resuspended in 100 µl of PBS containing 0.5 µg of the anti-cyclin D3 mAb (clone G107-565, mouse $IgG_1$; PharMingen cat. no. 14781) and 1% BSA and incubated for 2 hours at room temperature. The cells were then rinsed with PBS containing 1% BSA and incubated with the FITC-conjugated goat anti-mouse IgG antibody (Molecular Probes) diluted 1:30 in PBS containing 1% BSA for 30 min at room temperature in the dark. The cells were rinsed again, resuspended in 5 µg/ml of PI and 0.1% RNase in PBS and incubated at room temperature for 20 min prior to fluorescence measurements. Isotype-matched IgG (Sigma) was used as a control to define the background fluorescence. Detection of cyclins by flow cytometry was performed essentially as described in Juan et al., *Cell. Prolif.* 29:259–266 (1996); Gong et al., *Leukemia* 9:893–899 (1995); Darzynkiewicz et al., *Methods Cell Biol.* 41:421–435 (1994).

Fluorescence Measurements Cellular fluorescence was measured with the ELITE ESP flow cytometer/cell sorter (Coulter Inc., Miami, Fla.) using either an argon ion laser (emission at 488 nm) alone or combined with a helium-cadmium laser (emitting UV light). In the first case, fluorescence signals were collected using the standard configuration of the flow cytometer (green fluorescence, representing FITC labeled anti-$pRB^{P-}$ mAb; red fluorescence representing CYCHROME® tagged anti-$pRB^T$ mAb). In the second case, DNA content was analyzed based on DAPI fluorescence (blue emission) excited by UV light, while the anti-$pRB^{P-}$ mAb FITC-related emission and anti-$pRB^T$ CYCHROME®-related emission was excited with blue light laser. Unless noted, the procedures for multicolor measurement of cellular fluorescence and multivariate cell analysis were essentially as described in Juan et al., *Cell. Prolif.* 29:259–266 (1996) and Juan et al., *Exper. Cell Res.* 227:197–202 (1996). The experiments were repeated several times, on lymphocytes obtained from three different donors, yielding essentially identical results.

Results

Reactivity of lymphocytes with anti-$pRB^{P-}$ or with anti-$pRB^T$ mAbs during the initial 24 hours of their mitogenic stimulation by PHA is shown in FIG. 1. At zero time nearly all lymphocytes reacted with both antibodies, as it was evident by their fluorescence intensity exceeding the background level of the respective control cells. The mean fluorescence intensity of the cell population reacting with anti-$pRB^T$ mAb did not vary significantly during the stimulation, although somewhat increased intercellular variability was seen at 3 and 4 hours after addition of PHA. A great change, however, was observed, in reactivity of the cells with anti-$pRB^{P-}$ mAb. Namely, while at zero time and during the initial 2 hours of stimulation nearly all cells stained with anti-$pRB^{P-}$ mAb, two distinct subpopulations become apparent after 3 hours in the presence of PHA, one unreactive with anti-$pRB^{P-}$ mAb and another still stainable with this antibody, with similar intensity as at zero time. Between 4 and 12 hours a large fraction of lymphocytes (~80%) did not react with anti-$pRB^{P-}$mAb and at 24 hours proportions of the reacting and nonreacting cells were approximately similar.

Interestingly, the loss of reactivity with anti-pRB$^{P-}$ mAb observed between third and fourth hour of stimulation was abrupt, with no evidence of significant number of pRB$^{P-}$ positive cells showing decreased stainability with this antibody. The presence of the pRB$^{P-}$ epitope within the individual cells, thus, appears to be all or none phenomenon as reflected by absence of cells with intermediate level of pRB$^{P-}$. Since during the initial 24 hours of stimulation with PHA very few cells entered S phase (over 95% cells had a uniform, $G_{0/1}$ DNA content), the univariate pRB distributions rather than the bivariate (pRB vs. DNA) are shown in FIG. 1.

Essentially identical frequency histograms as these shown in FIG. 1 for pRB$^{P-}$ were obtained when the cells were stained with the mixture of anti-pRB$^{P-}$ (FITC) and anti-pRB$^T$ (CYCHROME®) mAbs and their fluorescence intensity ratios of pRB$^{P-}$ (FITC)/pRB$^T$ (CYCHROME®) rather than the fluorescence intensity related to pRB$^{P-}$ alone were plotted (not shown). The similarity, of course, is a reflection of the fact that the cells' reactivity with anti-pRB$^T$ mAb remained invariable during stimulation.

Frequencies of cells reacting with anti-pRB$^{P-}$ or anti-pRB$^T$ mAbs as well as these expressing cyclin D3 during lymphocyte stimulation are shown in FIG. 2. The frequency of cells reactive with anti-pRB$^T$ MAB was rather invariant, well over 80%, throughout all times of exposure to PHA. The percentage of anti-pRB$^{P-}$ mAb negative cells, however, varied markedly, decreasing from 98 to nearly 20% between 3 and 4 hours of stimulation, remaining at about 20% level up to 14 h, and then increasing, to reach 45% at 24 h.

The decrease in percentage of cells reacting with anti-pRB$^{P-}$ MAB coincided in time with the appearance of cells expressing cyclin D3 (FIG. 2). Over 98% of the nonstimulated lymphocytes did not react with anti-cyclin D3 mAb. The cyclin D3-positive cells, however, became apparent as early as 3 hours after addition of PHA, and their proportion was on steady rise afterwards, reaching nearly 70% at 12 h, and then declining to 40% at 24.

Figure 3:
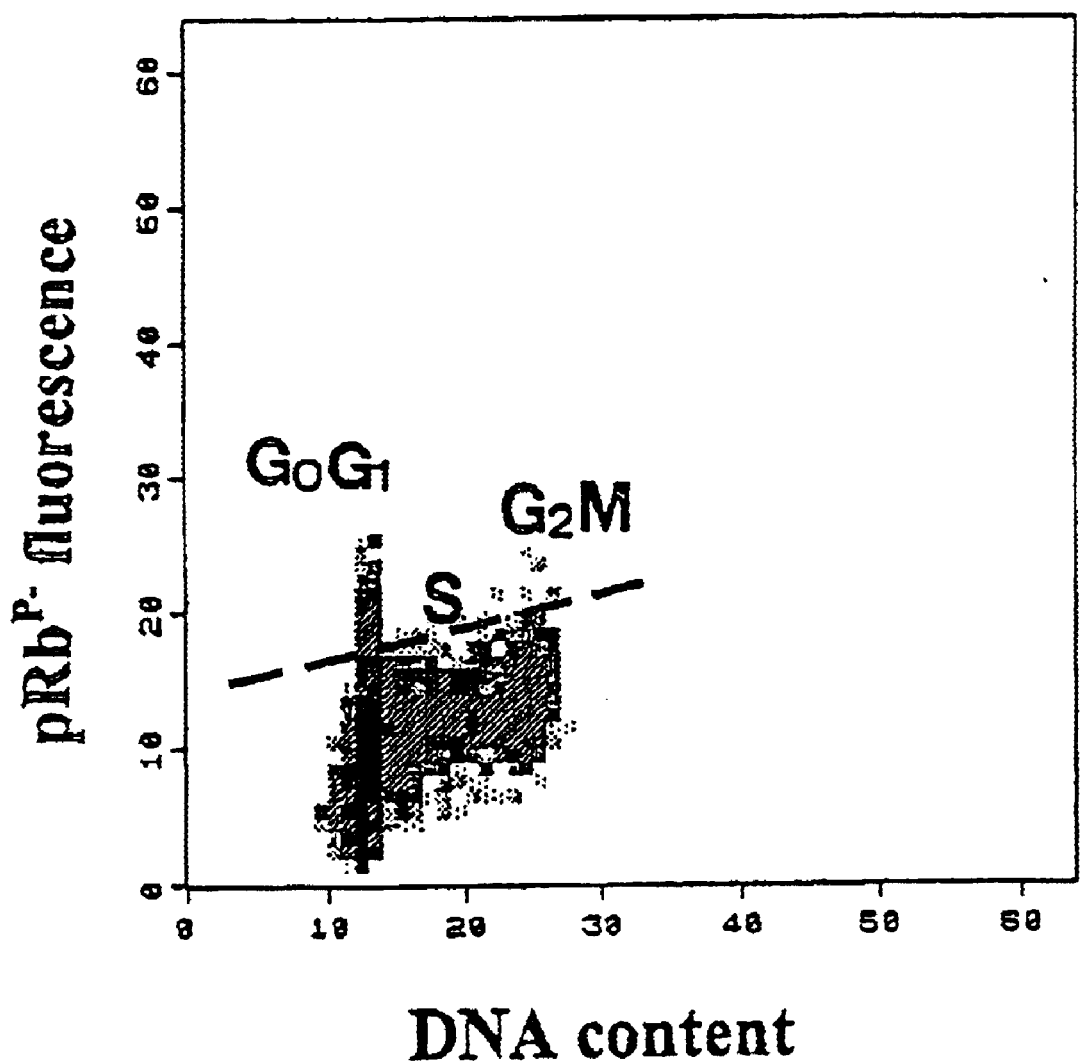
FIG. 3 shows bivariate distribution of DNA content vs. reactivity with anti-$pRB^{P-}$ mAb on the third day of lymphocyte mitogenic stimulation with PHA. The threshold (dashed line) represents the background fluorescence of the same cells stained with FITC labeled isotype-matched IgG1. Similar distribution was seen in cultures of PHA-stimulated lymphocytes maintained in exponential growth for 6 days in the presence of interleukin 2.

FIG. 3 shows the bivariate distribution of pRB$^{P-}$ vs. DNA content (cell cycle position) in a population of PHA-stimulated lymphocytes, 3 days after addition of the mitogen, i.e., when the cells were actively proliferating, distributed in all phases of the cycle. As is evident, relatively few pRB$^P$-positive cells were present in this culture. Nearly all cells reacting with anti-pRB$^{P-}$ mAb had a $G_0/G_1$ DNA content; the cells in S, $G_2M$, as well as most cells in $G_0/G_1$ phase were pRB$^{P-}$-negative. Analysis of the continuity of the isometric contour outlines of this bivariate distribution indicates that only early $G_1$ cells (and perhaps also $G_0$ cells, not responding to PHA) were reactive with anti-pRB$^{P-}$ mAb, while the $G_1$ cells just prior to entrance to S (in continuity with the S phase contour) were not stainable with this antibody.

Figure 4:
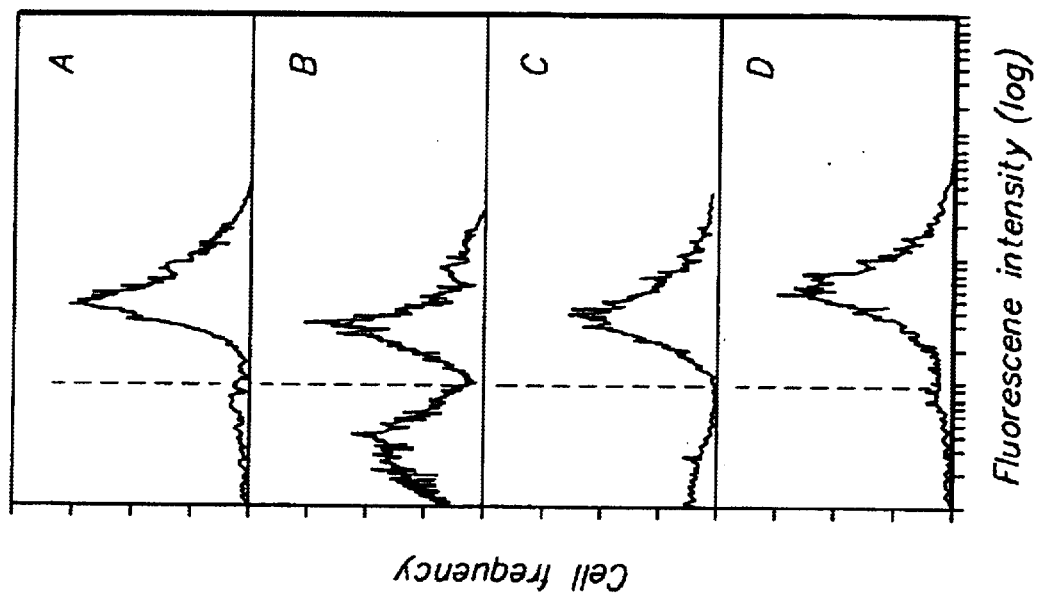
FIG. 4 shows the effect of pretreatment with alkaline phosphatase and effect of staurosporine (STP) added at time 0, together with PHA, on cell reactivity with anti-$pRB^{P-}$ mAb: panel A, unstimulated lymphocytes; panel B, lymphocytes stimulated with PHA for 24 h; panel C, lymphocytes stimulated for 24 hours but pre-incubated with alkaline phosphatase prior to incubation with anti-$pRB^{P-}$ mAb; panel D, lymphocytes stimulated with PHA for 24 hours in the presence of 20 nM STP. Note the loss of cell subpopulation unreactive with anti-$pRB^{P-}$ after treatments with STP (panel D) or phosphatase (panel C). Because the cell frequency coordinate scale varied between the samples (automatically adjusted by the software of the flow cytometer to present major peaks at similar heights) the apparent loss of the subpopulation unreactive with anti $pRB^{P-}$ mAb is not seen to be compensated by the increase in size of the peak representing the reactive population.

Specificity of anti-pRB$^{P-}$ mAb was examined by analyzing its binding ability following preincubation of cells with phosphatase; specificity was further examined by evaluating the effects of the non-specific protein kinase inhibitor staurosporine (STP; FIG. 4). As is evident, although exposure of the permeabilized cells to alkaline phosphatase had little effect on their subsequent stainability with anti-pRB$^T$ mAb, it changed their reactivity with anti-pRB$^{P-}$ mAb. Namely, the cell subpopulation unreactive with this antibody (from 24 hours PHA culture), which was present prior to incubation with the enzyme, was not apparent afterwards (FIG. 4). Likewise, preincubation with phosphatase rendered those subpopulations of cells from the 3 to 12 hour-stimulated PHA cultures which were initially unstainable with anti-pRB$^{P-}$ mAb, stainable with this antibody (not shown). The preincubation did not lead to the increase in the degree of stainability of either nonstimulated lymphocytes or of the subpopulation of cells from PHA cultures which were already stainable with anti-pRB$^{P-}$ prior to the preincubation (FIGS. 4B and 4C). As is also evident in FIG. 4, the presence of 20 nM of STP during culture with PHA precluded the appearance of the cell population unreactive with anti-pRBP$^-$ mAb.

It should be stressed that additional lines of evidence indicate that the anti-pRB$^{P-}$ mAb used in these studies interacts specifically with underphosphorylated pRB, while the anti-pRB$^T$ detects both underphosphorylated and phosphorylated forms of this protein. Thus, the. hybridoma clone G99-549, which secretes mouse mAb of IgG1 isotype against pRB$^{P-}$, was derived from a fusion for which underphosphorylated human pRB produced in Sf9 insect cells had been used as an immunogen. From the hybridoma clones positive for pRB in Western blots, only a single clone identified the underphosphorylated forms of p105$^{Rb}$. The epitope recognized by clone G99-549 was mapped to be between amino acids 514 and 610, which is located within "A box" of a large T-antigen binding pocket domain of human pRB. Most likely G99-549 mAb does not recognize an unphosphorylated phosphorylation consensus as such but rather a different structural conformation of pRB$^{P-}$.

Several earlier-performed control experiments show that the faster migrating forms of pRB recognized by this mAb were indeed lacking phosphorylation. Specifically: (i) when a control mAb (G3-245) that reacts with all forms of pRB (it recognizes an epitope between amino acids 300 and 380 of human pRB) was used with $^{32}$p-labeled cells, the ratio of labeled phosphorylated pRB to total pRB precipitated by G3-245 was over 100-fold greater than the ratio obtained with G99-549; (ii) when phosphorylated pRB was dephosphorylated by alkaline phosphatase in vitro the Western blot bands with G3-245 and G99-549 mAbs become similar; (iii) when all forms of pRB were immunoprecipitated with G3-245 mAb followed by Western blotting with G99-549 mAb, a specific band for faster moving pRB was obtained, and (iv) G99-549 mAb identified pRB specifically in pRB expressing Baculovirus-infected insect cells on Western blots, whereas mock-infected insect cells gave no specific signal for this antibody. Taken together, all these experiments show that G99-549 mAb binds selectively to the underphosphorylated form of human pRB while anti-pRB$^T$ mAb has no such specificity.

Discussion

A large body of evidence indicates that anti-pRb$^{P-}$ mAb is a specific marker of underphosphorylated pRb and that anti-pRb$^T$ detects both phosphorylated and underphosphorylated forms of this protein. The present results indicate that interactions of pRb within lymphocytes with anti-pRb$^{P-}$ and anti-pRb$^T$ mAbs were not mutually exclusive, i.e., the cells which were stainable with anti-pRb$^{P-}$ mAb also were reactive with anti-pRb$^T$ mAb. This was the case regardless whether the cells were incubated with the respective mAbs sequentially (not shown) or both antibodies were present during the incubation. This could not have been predicted a priori. The respective epitopes (between 514 and 610 amino acids for anti-pRb$^{P-}$P and between 300 and 380 for anti-pRb$^T$), thus, appear not to spatially overlap to any significant degree which would interfere with simultaneous binding of both mAbs to underphosphorylated pRb, i.e., resulting in a steric hindrance.

The present data show that pRB phosphorylation during lymphocyte stimulation occurs as early as 3 hours after addition of PHA, is rapid and total, and affects nearly all pRB molecules within each individual cell. The latter conclusion is drawn from the observation of discontinuous, quantum-like loss of the cells' stainability with the anti-pRb$^{P-}$ mAb, manifested by the absence of cells characterized by intermediate reactivity with this antibody at any time during the stimulation. The observation that preincubation with phosphatase did not additionally increase reactivity of the already pRb$^{P-}$ positive subpopulation of lymphocytes in PHA cultures with the antibody (FIG. 2) gives further support to this conclusion.

Simultaneous analysis of the same cells using the combination of anti-pRb$^{P-}$ and anti-pRb$^T$ mAbs made it possible to ascertain that the observed loss of reactivity of with anti-pRb$^{P-}$ indeed reflected pRB phosphorylation rather than a decrease in cellular content of this protein. Because the reactivity with anti-pRb$^T$ mAb during lymphocyte stimulation was rather constant (FIGS. 1 and 3), the fractions of cells recognized as having underphosphorylated pRB based on their labeling with anti-pRb$^{P-}$ mAb alone (FIG. 1) or by the ratio of pRb$^{P-}$/pRb$^T$ (each labeled with different color fluorochrome, not shown) were essentially the same. The ratiometric analysis of pRb$^{P-}$/pRb$^T$, however, is essential when pRB phosphorylation within cells having different levels of total pRB must be compared.

During $G_1$ phase, pRB is phosphorylated by Cdk4 and in some cell types also by Cdk6. In the case of lymphocytes, Cdk4 is activated by cyclins D2 and D3. The initiation of pRB phosphorylation during lymphocyte stimulation, seen 3 hours after addition of the mitogen (FIG. 1), coincided with the appearance of cells expressing cyclin D3 (FIG. 2). Further increase in the percentage of cyclin D3-positive cells, however, was delayed as compared to the drop in the percentage of cells reactive with anti-pRb$^{P-}$ mAb. It is possible that either a minor level of cyclin D3 (immunocytochemically undetectable) was already adequate to activate Cdk4, or that induction of cyclin D2 by PHA preceded the appearance of cyclin D3 during the stimulation. Indeed, the data in the literature suggest that during lymphocyte stimulation, induction of cyclin D2, detected by Western blotting, may occur just prior to the induction of cyclin D3.

Phosphorylation of pRB in PHA-stimulated lymphocytes was prevented by STP (FIG. 4). It has previously been shown that STP arrests lymphocytes and fibroblasts early in $G_1$, past the point of induction of cyclins D3 and D2 but prior to induction of cyclin E. Fibroblasts and cells of human lung or breast cancer lines arrested in $G_1$ by STP have underphosphorylated pRB. The possible target of STP in all these cells may thus be Cdk4. Recent data, however, suggest that the STP-induced arrest in $G_1$ may be associated with the induction and accumulation of p18 and p27$^{KIP}$ Cdk inhibitors.

Multiparameter analysis of pRb$^{P-}$ vs. DNA content (FIG. 3) or pRb$^-$/pRb$^T$ ratio, as offered by the present approach, enables one to analyze the status of pRB phosphorylation in relation to the position of the cell in the cycle in asynchronous, exponentially growing cell populations, obviating their synchronization. Cell synchronization by inhibitors of DNA replication, which is necessary in the case of tumor cells (which unlike normal cells cannot be synchronized by withdrawal of growth factors or serum) or in the case suspension cultures which cannot be synchronized by mitotic detachment, introduces experimental bias due to induction of a severe imbalance of cyclin expression. The present approach, therefore, may be uniquely suitable to assay status of pRB phosphorylation in individual cells but without perturbing their progression through the cycle.

Certain cell features, such as cellular RNA content, nucleolar mass, chromatin structure (degree of condensation), expression of Ki-67 antigen, or other proliferation-associated proteins have been repeatedly proposed as markers distinguishing cycling from noncycling cells. However, there is no generally accepted, easily measurable marker, which discriminates $G_0$ from $G_1$ cells. The present methods and results for the first time make possible the use of pRB phosphorylation as such a marker. Since pRB phosphorylation commits the cell to enter S phase, the cells with a $G_{0/1}$ DNA content having hyperphosphorylated pRB can be classified as $G_1$, while the cells with underphosphorylated pRB, as $G_0$.

Antitumor drug development is now focused on agents which target Cdk4 or other Cdks to stop their pRB phosphorylating activity. The simple assay of pRB phosphorylation, as shown here to demonstrate the effect of STP (FIG. 4), can be conveniently used to rapidly screen activity of such agents. Because the assay utilizes intact cells rather than cell extracts, the permeability of the studied agents through the plasma membrane is screened at the same time. Most important, however, because individual cells are analyzed, it makes it possible to estimate the intercellular variability and detect rare cells or cell subpopulations with different properties. This is of special importance in light of the evidence of heterogeneity of tumor cell populations and the fact that most tumor cells are generally eradicated during the treatment; it would be of great interest to identify the few cells which survive and are responsible for the relapse. Furthermore, multiparameter analysis offers a unique opportunity to correlate the status of pRB phosphorylation either with expression of other proteins (identified immunocytochemically) or with DNA replication (detected, e.g., by BrdU incorporation) on the cell by cell basis. The methodology, therefore, can find wide use in screening new anti-tumor drugs targeting Cdks. It can also be of use to characterize populations of tumor cells with respect to pRB phosphorylation status, as a possible prognostic market in oncology.

Example 2

Flow Cytometric Measurement of pRB Protein Phosphorylation in HL-60 Cells During Proliferation and Differentiation Cells The human promyelocytic leukemic cell line HL-60 was kindly provided by Dr. Harry A. Crissman of the Los Alamos National Laboratory (Los Alamos, N.Mex.). The cells were maintained in RPMI 1640 supplemented with 10% fetal calf serum, 100 units/ml penicillin, 100µg/ml streptomycin, and 2 mM L-glutamine at a density between 2 and 8×10$^5$ cells/ml at 37.5° C. in the mixture of 95% air and 5% $CO_2$ for the periods of time described in the legends to the respective figures. During the exponential phase of cell growth, at densities below 8×10$^5$ cells/ml, the mean duration of the cell cycle of these cells is 23 hours (estimated as described in Darzynkiewicz, "Mammalian cell cycle analysis," in *The Cell Cycle: A Practical Approach*, P. Fantes and R. Brooks, Eds., pp. 45–68 (Oxford Univ. Press, Oxford, UK, (1993)), and the mean duration of $G_1$, S, $G_2$, and M 11, 9, 2, and 1 h, respectively. The medium, supplements, and antibiotics were obtained from Life Technologies (Grand Island, N.Y.).

All-trans retinoic acid (RA), 1,25-dihydroxy vitamin D3 (vitamin $D_3$), and phorbol myristate acetate (PMA) were purchased from Sigma Chemical Co. (St. Louis, Mo.). Stock solutions of RA and vitamin D3 at 1 mM concentration were prepared in ethanol and stored at −70° C. in the dark for up to a month. RA and vitamin $D_3$ were included into cultures at a final concentration of $5 \times 10^{-7}$ M and $10^{-8}$ M, respectively. Control cells were treated with an equivalent concentration of ethanol (<0.02%). Stock solution of PMA at 1.6 mM was prepared in DMSO, stored at −20° C. in the dark, and used at a final concentration of $4 \times 10^{-8}$ M. The cultures were kept shielded from light. Unless stated otherwise, the cultures were treated with RA for 5 days, with vitamin $D_3$ for 6 days, and with PMA for 24 h. The cells that become attached to the flasks during differentiation were removed from the flasks mechanically by rubber policeman and pooled with the cells floating in the culture media.

Immunocytochemical Detection of $pRB^T$ and $pRB^{P-}$

Methods were essentially as described in Example 1. Briefly, the cells were fixed in suspension in 1% formaldehyde in PBS for 15 min on ice, then washed with PBS, and resuspended in ice-cold 80% ethanol for up to 24 h. After fixation, the cells were washed twice with PBS and then suspended in 1 ml of 0.25% Triton X-100 in PBS on ice for 5 min. After centrifugation, the cell pellet was suspended in 100 μl PBS containing 1% bovine serum albumin (BSA; Sigma) and 0.5 μg of the anti-$pRB^T$ mAb (PharMingen, clone G3-245) conjugated with CYCHROME® and/or with 1 μg of anti-$pRB^{P-}$ mAb (PharMingen, clone G99-549) conjugated with FITC and incubated for 2 h at room temperature. The cells were then rinsed with PBS containing 1% BSA, counterstained with 4,6-diamidino-2-phenyl indole (DAPI) (Molecular Probes Inc., Eugene, Oreg.), and their fluorescence was measured by flow cytometry.

To demonstrate specificity of the mAbs with respect to pRB phosphorylation, prior to incubation with the mAbs the cells in control experiments were preincubated with 4 units of alkaline phosphatase (type VII from bovine intestinal mucosa; Sigma) in 100 μl of Tris buffer (Sigma) at pH 9.4 for 30 min. Other controls consisted fluorochrome-conjugated isotype matched tagged mAb to irrelevant antigen (IgG1; clone MOPC-21, PharMingen).

Fluorescence Measurements

Cellular fluorescence was measured with the ELITE ESP flow cytometer/cell sorter (Coulter Inc., Miami, Fla.) using an argon ion laser (emission at 488 nm) combined with a helium-cadmium laser (emitting UV light). DNA content was analyzed based on DAPI fluorescence (blue emission) excited by UV light, while the anti-$pRB^{P-}$ mAb (FITC)-related emission and anti-$pRB^T$ (CYCHROME®)-related emission was excited with blue light laser. To obtain the mean fluorescence values as shown in FIGS. 7–10, the cells were gated based on differences in their DNA content to distinguish cells in G1, S, and $G_2$/M, and from the mean values of the FITC fluorescence the mean value of the respective control cells (FITC-conjugated isotype-matched IgG1) in the same phase of the cycle was subtracted. The mean values of S phase cells were multiplied by 0.75 and of $G_2$/M cells by 0.5 to express the pRB-associated cell fluorescence per unit of DNA. The data were normalized to the mean fluorescence value of $G_1$ cells from the untreated, control culture. (100), as shown in FIGS. 7–10. The experiments were repeated, inducing cell differentiation by each of RA, vitamin $D_3$, and PMA at least three times, with essentially identical results.

Immunoblotting

To reveal specificity of the antibodies used in these experiments, a standard Western blotting procedure was used on cellular lysates, as described in Gong et al., *Cell Growth Differ.* 6:1485–1493 (1995).

Results

Figure 5:
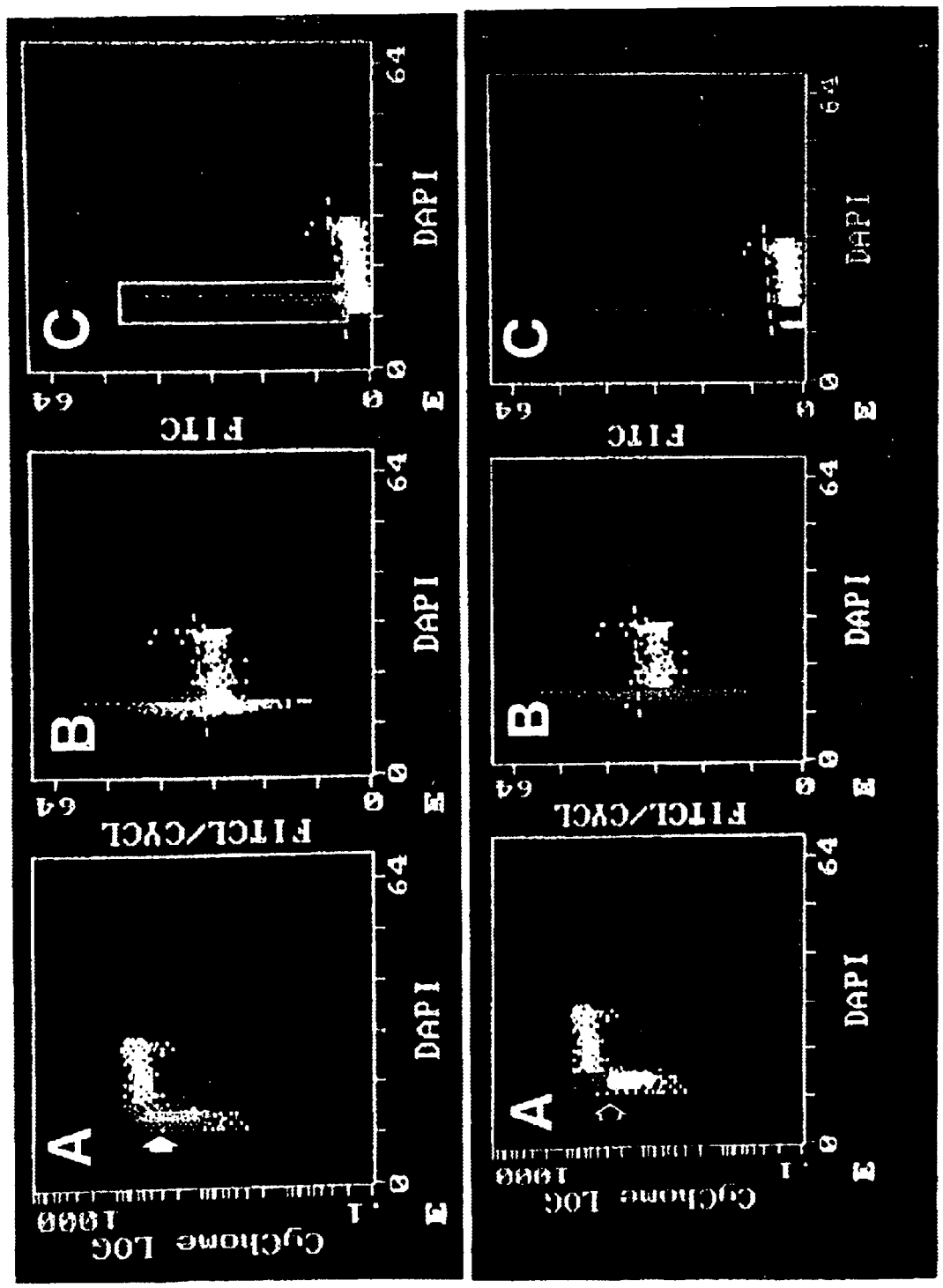
FIG. 5 presents bivariate distributions of HL-60 cells from the control culture showing expression of $pRB^T$ CYCHROME®, A panels), the $pRB^{P-}/pRB^T$ ratio (FITC/CYCHROME®, B panels), and $pRB^{P-}$ (FITC, C panels) versus cellular DNA content (DAPI). The three top panels show gating analysis of $pRB^{P-}$ positive cells, and the bottom three panels show gating analysis of $G_1$ cells expressing high (suprathreshold) levels of $pRB^T$. Variability of $G_1$ cell population with respect to $pRB^T$ is evident in panels A (note that the CYCHROME® scale is exponential). Arrows indicate a threshold representing minimal $pRB^T$ level of S phase cells; $G_1$ cells with a subthreshold $pRB^T$ level do not enter S phase. Panel C, top, shows the gate used to select the cells which have hypophosphorylated pRB ($pRB^{P-}$ positive cells; the dashed line indicates mean FITC fluorescence +3 SD of the cells stained with the same mAb but after treatment with alkaline phosphatase). The gated $pRB^{P-}$ positive cells, color labeled (green), show variable levels of $pRB^T$ when revealed in panel A and have a $pRB^{P-}/pRB^T$ ratio above the threshold value, greater than that of S phase cells (B). The $G_1$ cells with high $pRB^T$ values, above the threshold, gated as shown in panel A, bottom (marked in red), show variable $pRB^{P-}/pRB^T$ (panel B) and $pRB^{P-}$ (panel C); some of these cells are $pRB^{P-}$ positive, others negative (C)

FIG. 5 presents the bivariate distribution of $pRB^T$, $pRB^{P-}$, and $pRB^{P-}/pRB^T$ versus the cellular DNA content of proliferating HL-60 cells. Because the measurement of DNA content reveals the cell cycle position, the bivariate analysis as shown in this figure allowed us to correlate expression of total pRB as well as its phosphorylation state ($pRB^{P-}$, $pRB^{P-}/pRB^T$) with the cell cycle phase of individual cells. As is evident, the $G_1$ cell population was characterized by great intercellular variability in expression of $pRB^T$. Also, a threshold in $pRB^T$ during $G_1$ was apparent, namely, nearly all cells entering S, as well as the cells in S and $G_2$/M, expressed $pRB^T$ above the threshold level (FIG. 5A, arrow). Actually, the absence of cells with the subthreshold $pRB^T$ that would be in S or $G_2$/M was a very characteristic and consistent feature of all the $pRB^T$ versus DNA content distributions, whether representing cells from the untreated or differentiating cultures.

Figure 6:
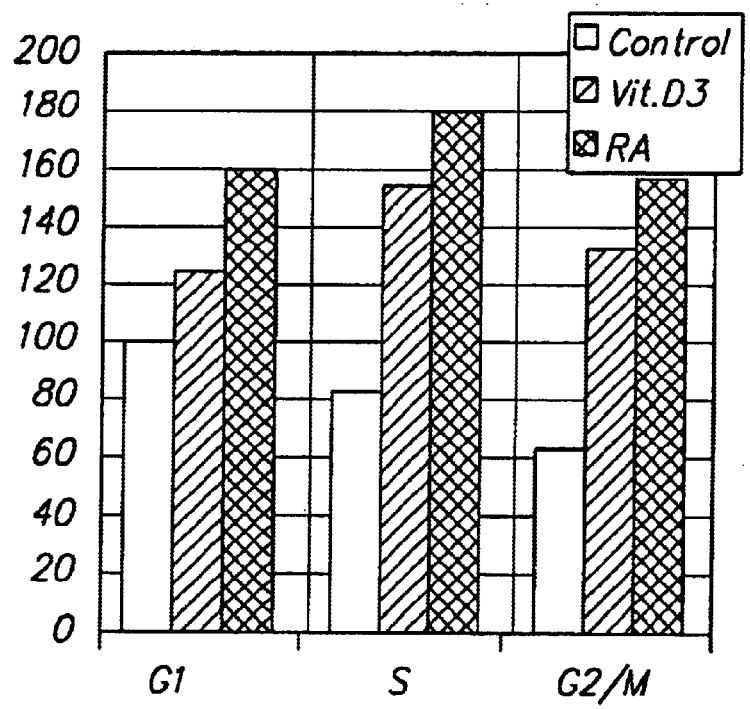
FIG. 6 shows changes in $pRB^T$ during differentiation of HL-60 cells. The bars represent mean $pRB^T$ fluorescence of $G_1$, S, and $G_2$/M cells from the control cultures and from the cultures treated with RA or vitamin $D_3$, calculated as described under Material and Methods for Example 2. $G_1$, S, and G2/M cells were distinguished and gated based on differences in their DNA content, their mean $pRB^T$ fluorescence is expressed per unit of DNA and normalized to the mean fluorescence of $G_1$ cells from the control culture, which was expressed as 100.

The mean $pRB^T$ per cell was increasing during S and $G_2$ in the control cultures: the cells in $G_2$/M bound about 30% more $pRB^T$ mAb than the $G_1$ cells. However, when $pRB^T$ expression was calculated per unit of DNA, a reduction by about 40% was observed for $G_2$/M cells compared to cells in $G_1$ (FIG. 6). Unlike $G_1$ cells, the cells in S and $G_2$/M were much more uniform in terms of $pRB^T$ expression (FIG. 5).

Figure 7:
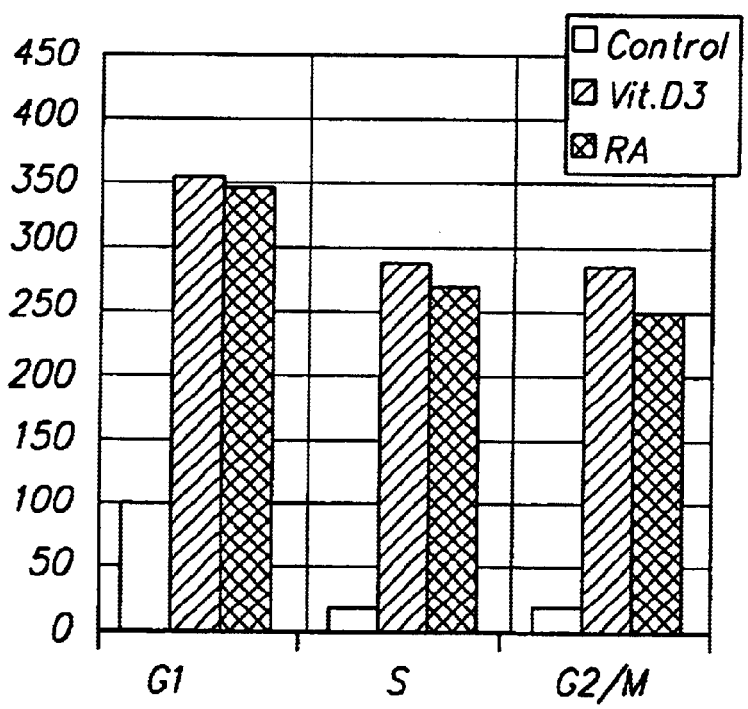
FIG. 7 shows changes in $pRB^{P-}$ during differentiation of HL-60 cells. The bars represent mean values of $pRB^{P-}$ fluorescence of the control cells and the cells from vitamin $D_3$ and RA-treated cultures estimated for $G_1$, S, and $G_2$/M cells, as described in the legend to FIG. 6 and in Example 2, below.
Figure 8:
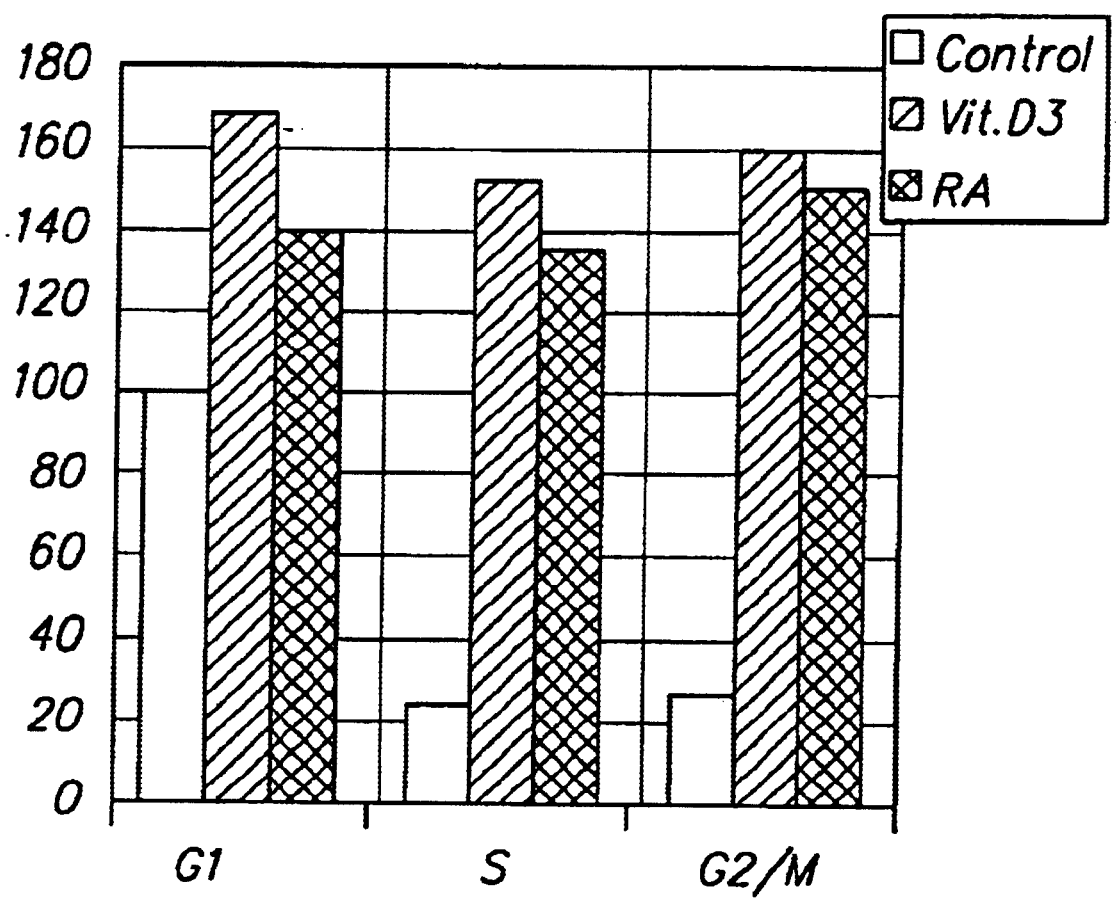
FIG. 8 demonstrates changes in $pRB^{P-}/pRB^T$ during differentiation of HL-60 cells. The bars represent mean values of $pRB^{P-}/pRB^T$ ratio estimated for $G_1$, S, and $G_2$/M cells from control and vitamin $D_3$ and RA-treated cultures.

In the exponentially growing, untreated cultures, the expression of $pRB^{P-}$ was confined to a fraction of $G_1$ cells (FIG. 5). This fraction was rather small: In numerous cultures of exponentially growing HL-60 cells (n=6) the mean frequency of $G_1$ cells expressing $pRB^{P-}$ was 11/8% (±4.5; SD). When calculated per all cells, including S and $G_2$/M, the fraction of $pRB^{P-}$ positive cells was only 5.5±2.8%. Because expression of $pRB^{P-}$ in individual S or $G_2$/M cells was minimal, the mean value of $pRB^{P-}$ of the cells traversing these phases was much lower compared to $G_1$ cells (FIG. 7). The very few $pRB^{P-}$-positive cells with a $G_2$/M DNA content that were revealed on the scattergrams are likely to be the doublets of $G_1$ cells.

Figure 9:
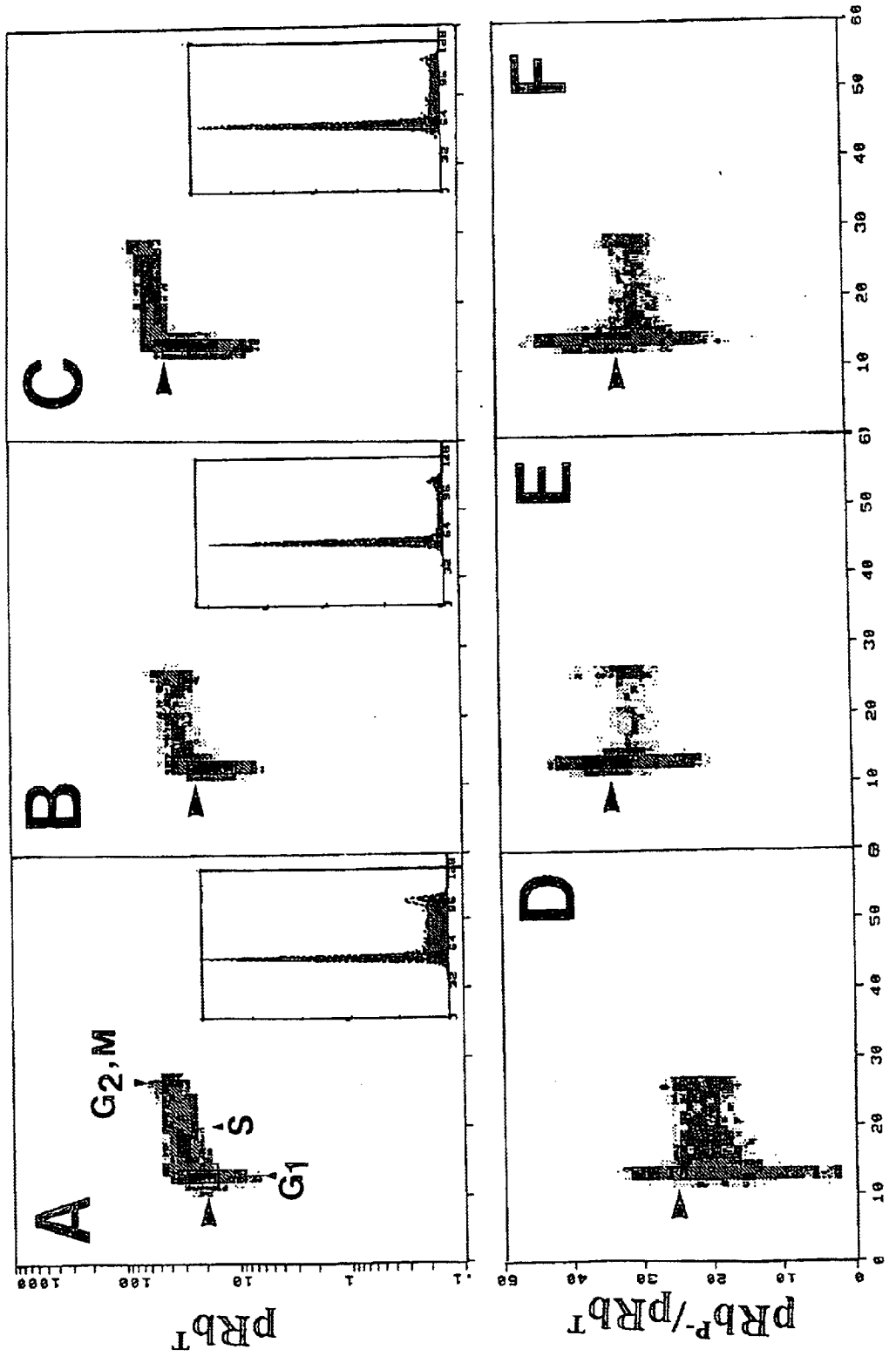
FIG. 9 shows bivariate distributions of $pRB^T$ and $pRB^{P-}/pRB^T$ versus cellular DNA content of exponentially growing cells from untreated cultures (panels A and D) and cultures treated with RA (panels B and E) and with vitamin $D_3$ (panels C and F), obtained as described under Material and Methods for Example 2. The mean $pRB^T$ fluorescence of cells from the differentiating cultures is increased (note that the $pRB^T$ scale is exponential). Also increased is their $pRB^{P-}/pRB^T$ ratio. The arrowheads indicate the threshold levels of $pRB^T$ or $pRB^{P-}/pRB^T$ representing minimal $pRB^T$ and maximal $pRB^{P-}/pRB^T$ of early S phase cells, respectively.

The above-discussed cell cycle phase-related differences in $pRB^T$ and $pRB^{P-}$ were reflected in the change of $pRB^{P-}/pRB^T$ across the cell cycle (FIGS. 5 and 9). The intercellular variability of the $G_1$ population with respect to $pRB^{P-}/pRB^T$ and the presence of a $pRB^{P-}/pRB^T$ threshold prior to entrance to S were both evident. The cells in S and $G_2$/M were much more uniform in their $pRB^{P-}/pRB^T$ ratio than $G_1$ cells.

Color gating ("paint-a-gate" analysis) was performed to reveal a possible correlation between the cellular level of pRB and state of its phosphorylation vis-à-vis the cell cycle position. The first "gate" was chosen to select $G_1$ cells that were reactive with anti-$pRB^{P-}$ (FIG. 5C, top). As is evident, the cells selected within this gate were characterized by variable level of $pRB^T$: some of them had subthreshold, others suprathreshold levels of $pRB^T$. Another gate was chosen to select $G_1$ cells that had maximal (suprathreshold) $pRB^T$, similar to that of S phase cells. (FIG. 5A, bottom). Being contiguous with the S phase cell cluster on the $pRB^T$ versus DNA content bivariate scattergrams, this gate represents the compartment from which the cells enter S. This cell population was variable with respect to $pRB^{P-}$: some cells reacted with anti-$pRB^{P-}$ mAb, others did not (FIG. 5C, bottom). The gating analysis thus revealed that expression of pRB and the state of its phosphorylation in $G_1$ cells were not correlated: The cell population uniform in $pRB^T$ (with maximal level of this protein) was heterogenous with respect to $pRB^{P-}$, while the population of $pRB^{P-}$-positive cells was heterogenous with respect to $pRB^T$. This was the case for both the untreated (FIG. 5B) and the vitamin $D_3$- or RA-treated (not shown) cells. As would be expected, the $pRB^{P-}/pRB^T$ of the $pRB^{P-}$-positive cells was above the threshold level of the S phase cells (FIG. 5B, top), and, as the pattern of cell distribution on the bivariate scattergrams indicates, these cells were not directly entering S.

Figure 10A:
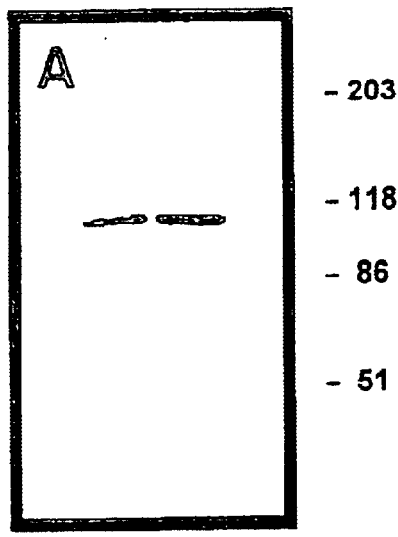
FIG. 10 presents a Western blot showing reactivity of anti-$pRB^{P-}$ mAb(A) and anti-$pRB^T$ mAb with proteins extracted from control (CON) and PMA-treated cells. Note the increased intensity bands representing hypophosphorylated pRB (panel A, also bottom band in B), hyperphosphorylated pRB (top band in B), and total pRB (both bands in B)
Figure 10B:
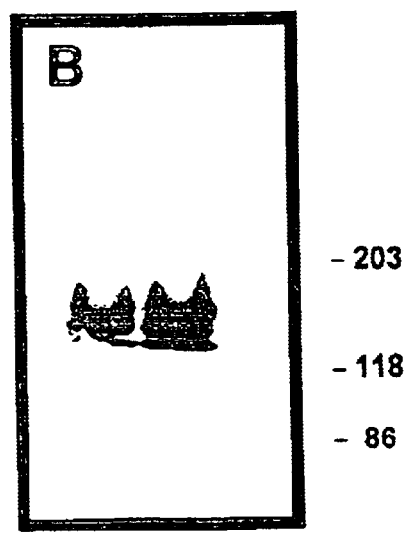

FIGS. 6–9 illustrate changes in $pRB^T$ and $pRB^{P-}$ in HL-60 cells undergoing differentiation following treatment with RA or vitamin $D_3$. Similar changes were also observed in the case of cells induced to differentiation by PMA (not shown). The treatment led to an increase in the proportion of cells in $G_{0/1}$ coinciding with a decrease of S and $G_2/M$ cells (FIG. 9). The differentiating cells showed, on average, increased $pRB^T$ compared to the cells from the control cultures. The increase was greater for S and $G_2/M$ cells than for $G_{0/1}$ cells (FIG. 6). The increase was also apparent from the Western blots (FIG. 10). Thus, for example, the S and $G_2/M$ cells in the RA- or vitamin $D_3$-treated cultures had nearly twofold higher $pRB^T$ than their respective counterparts from the untreated cultures. On the other hand the $G_{0/1}$ cells from differentiating cultures showed only a 20 (for vitamin $D_3$) or a 60% (for RA) increase (FIG. 6). Furthermore, the threshold in $pRB^T$ during $G_{0/1}$ was more pronounced in populations of cells from the vitamin $D_3$- or RA-treated cultures. The prominence of the threshold was due to the fact that the $G_{0/1}$ cell population with the subthreshold level of $pRB^T$ was more numerous and more heterogenous, in terms of $pRB^T$ expression, than that of the $G_1$ cells from the untreated cultures.

Cells from the vitamin $D_3$- or RA-treated cultures also had increased $pRB^{P-}$ (FIG. 7). The increase in $pRB^{P-}$ observed after induction of differentiation, however, was greater than the rise in $pRB^T$. Thus, for example, whereas the increase in $pRB^{P-}$ for $G_{0/1}$ cells was 20 or 60% (for vitamin $D_3$- or RA-treated cells, respectively), the increase in $pRB^{P-}$ was fourfold. The increase was even greater for S and $G_2/M$ phase cells, which had over an order of magnitude higher levels of $pRB^{P-}$ than their counterparts from control cultures.

These changes in $pRB^T$ and $pRB^{P-}$ during differentiation were reflected by altered $pRB^{P-}/pRB^T$ ratios (FIGS. 9 and 10). Because the relative increase in $pRB^{P-}$ in the cells from RA- or vitamin $D_3$-treated cultures was greater than the increase in $pRB^T$, the $pRB^{P-}/pRB^T$ ratio of cells from the treated cultures was higher than that from the untreated cells. This was especially pronounced for S and $G_2/M$ phase cells, whose $pRB^{P-}/pRB^T$ level was over fivefold higher than that in control.

Discussion

The aim of this study was to analyze expression of pRB and reveal the state of its phosphorylation in individual cells during the cell cycle as well as after induction of differentiation. This was accomplished by taking advantage of a methodology which offers the possibility of directly correlating measurements of $pRb^T$ and $pRb^{P-}$ or their ratio with the cell cycle position. The study revealed several new findings pertaining to regulation of pRb accumulation in the cycle, as well as its phosphorylation.

The great intercellular variability of the $G_1$ population with respect to pRb expression, as observed, is due to the fact that the major increase in the cellular level of this protein that occurs in the cell cycle takes place during $G_1$ rather than throughout the remainder of the cycle. This was evident from the mean increase of $pRb^T$, which was minor during S and $G_2/M$ (~30%) and actually was negative (−40%) when expressed per unit of DNA (FIG. 6). Considering that the duration of $G_1$ of our cells is 13 hours and nearly equals the combined duration of S, $G_2$, and M (12 h; see Material and Methods), the data indicate that the rate of pRb accumulation (which may reflect either its increased synthesis or decreased degradation) is greater in $G_1$ than during the rest of the cycle.

Interestingly, a distinct threshold in $pRb^T$ was observed in $G_1$, as the cells with low level of this protein did not enter S. The G1 threshold in pRb also was observed by Stokke et al., who measured expression of this protein by flow cytometry. A similar threshold in G1 was earlier described for cellular RNA and protein content. Thus, similar to regulation of cellular RNA and protein content during the cell cycle, a regulatory mechanism may exist with respect to pRb, sensing cellular content of this protein and preventing cells with subthreshold pRb levels from initiating DNA replication.

In control, nondifferentiating cultures, the presence of hypophosphorylated pRb was detected in 11.8% of $G_1$ cells (5.5% of all cells in the culture). The remaining G1 cells as well as cells in S and $G_2/M$ were $pRb^{P-}$ negative. Because pRb is known to be dephosphorylated at mitosis, the daughter cells are expected to inherit hypophosphorylated pRb. The mean duration of the cell cycle ($T_c$) of our cells is 23 h. Taking into an account the cell-age distribution in exponentially growing cultures, duration of the time during which pRb was underphosphorylated can be derived from the formula $$\frac{t_{P-}}{T} = \frac{\ln(1 + f_{P-})}{\ln 2} \qquad (1)$$

where $t_{P-}$ is length of time when pRb remains underphosphorylated; T, duration of the cell cycle; and $f_{P-}$, fraction of cells with hypophosphorylated pRb. According to this equation, the $t_{P-}$ of our HL-60 cells during their exponential phase of growth was 1.8±0.9 h (n=6). Thus, pRb remained in hypophosphorylated state only for about 16±8% of the duration of $G_1$.

In exponentially growing, control cultures nearly 90% of $G_1$ cells, as well as all S and $G_2/M$ cells, showed no evidence of the presence of hypophosphorylated pRb. Phosphorylation of pRb in G1, thus, was total, affecting all molecules within the cell. Interestingly, however, no correlation between the cellular level of pRb during $G_1$ and the state of its phosphorylation was observed (FIG. 5). The cells with hypophosphorylated pRb had highly variable levels of total pRb. Likewise, the subpopulation of $G_1$ cells uniform with respect to $pRb^T$ (gated to select the cells with maximal total pRb, equivalent of S early phase cells) was heterogenous, consisting of cells with variable level of hypophosphorylated pRb (FIG. 5B). Based on these observations it is tempting to speculate that when postmitotic cells enter $G_1$ all their pRb is in hypophosphorylated state and that pRb phosphorylation is initiated shortly after mitosis. The rate of pRb phosphorylation within individual cells, however, is relatively slow and it takes, on average, 1.8 hours to achieve phosphorylation of nearly all pRb molecules. This rate is determined by the complex machinery regulating activation of Cdk4, which involves its phosphorylation, association with D type cyclins, and interaction with a plethora of Cdk inhibitors. New pRb is being synthesized as well, and it also undergoes phosphorylation at that time. Such a sequence of events provides an explanation for the apparent lack of correlation between the degree of pRb phosphorylation and the total level of this protein, as observed. It also is consistent with the observed heterogeneity of $G_1$ cells with respect to degree of pRb phosphorylation.

Phosphorylation of pRb during $G_1$ is gradual and sequential, initially carried out by cyclin D/Cdk4 and subsequently, affecting other pRb sites, by cyclin E/Cdk2. It is possible that conformation of pRb following phosphorylation by cyclin D/Cdk4 is different than conformation of this protein after phosphorylation of the additional sites by cyclin E/Cdk2. The anti-pRb$^{P-}$ mAb used in the present study detects pRb for only a short period of time (1.8 h) during $G_1$, well before entrance of the cells to S, i.e., prior to the expected activation of cyclin E/Cdk2. In our previous study we observed that this mAb stops to recognize pRb 4 hours after mitogenic stimulation of lymphocytes, after induction of cyclins D2 and D3 but several hours before induction of cyclin E. The presently used pRb$^{P-}$ mAb, therefore, recognizes hypophosphorylated pRb prior to its phosphorylation by cyclin D/Cdk4 and is nonreactive with pRb which is phosphorylated either by cyclin D/Cdk4 or by cyclin D/Cdk4 followed by cyclin E/Cdk2.

The present data indicate that regardless whether differentiation of HL-60 cells was induced along a myelogenous pathway, as in the presence of RA, or along a monocytic pathway, as by vitamin D3 or PMA, the hypophosphorylated pRb predominated over its hyperphosphorylated form within individual cells. This observation is in agreement with the vast amount of data in the literature that indicates that pRb becomes hypophosphorylated during differentiation of cells of various lineages. Likewise, the observed rise in total pRb per cell as reflected by the increased binding of anti-pRb$^T$ is concordant with the published data showing that expression of this protein increases during cell differentiation regardless of the cell system. Inhibition of pRb phosphorylation observed during differentiation is attributed to suppression of Cdk4/6 activity through downregulation of D type cyclins, unregulation of Cdk inhibitors, as well as the upstream changes in growth factor receptors or signal transduction, affecting the pRb pathway.

The cause-effect relationship between the increased cellular level of pRb and differentiation was demonstrated by several observations. As mentioned, a close correlation has been reported between expression of pRb and cell differentiation in cells of different lineages. Furthermore, the decrease in expression of pRb enforced either by using the antisense strategy or by deletion of the RB gene invariably led to a loss in the cells' ability to differentiate. Conversely, induction of pRb overexpression was seen to trigger cell differentiation in several cell systems. It was not surprising, therefore, to observe in the present study that expression of pRb$^T$ was increased in the cells treated with RA, PMA, or vitamin $D_3$. The decrease in pRb$^T$ at late stages of differentiation, as reported by some authors, may be associated with cell apoptosis rather than differentiation per se, because it occurs late during differentiation, at the time when apoptotic cells are expected to be present. Degradation of pRb, mediated by caspases is known to occur during apoptosis, preceding chromatin condensation and internucleosomal DNA fragmentation. However, no significant apoptosis was observed during differentiation induced by vitamin $D_3$.

Our present data show that while the increase in total pRb during differentiation occurs in all phases of the cycle, its accumulation in a hypophosphorylated state is more pronounced during $G_1$. The increased level of pRb during cell differentiation, as observed in all the tissues studied thus far, may serve the function of effective sequestering of E2F transcription factors to prevent cell entrance to S. Namely, since interactions between pRb and E2F are expected to follow the chemical law of mass action, an excess of pRb, in its hypophosphorylated form, is required to maximally sequester all E2F within the cell and thereby prevent its binding to chromatin that otherwise may result in activation of the genes needed for cell passage through the $G_1$ restriction point. The mechanism of cell cycle arrest either in $G_{0/1}$ or partial arrest in $G_2$ during terminal differentiation thus may involve both synthesis of new pRb and dephosphorylation of pRb already present in the cell to provide a large pool of pRb in hypophosphorylated state. A theoretical model describing such a mechanism was recently developed by Kohn. It should be mentioned, however, that the mechanism of pRb action also may involve direct changes in chromatin structure via recruitment of histone deacetylase to E2F resulting in repression of the gene encoding for cyclin E.

As is evident from their reactivity with pRb$^{P-}$mAb or a high pRb$^{P-}$/pRb$^T$ ratio, the S and $G_2$/M cells from differentiating cultures, similar to $G_{0/1}$ cells, contained a significant proportion of pRb in a hypophosphorylated state. Thus, unlike in control cultures where all pRb within the cell undergoes phosphorylation prior to S, the cells induced to differentiation initiate DNA replication and progress through S having a significant proportion of pRb molecules in a hypophosphorylated state. Because of the higher total pRb level in the differentiating cells, compared to the control, phosphorylation of only a fraction of pRb molecules may be sufficient to release enough E2F to activate transcription of the genes committing the cell to enter S phase. If this is the case then the overall pRb level within the cell as well as its state of phosphorylation both are critical for cell commitment to enter S phase. The pRb level may be regulated at the stage of its transcription, translation, and/or degradation, while pRb phosphorylation in $G_1$ involves activation of Cdk4/6. Interestingly, it has been observed that development of cells, resistance to vitamin $D_3$ is associated with high levels of pRb, which remains hyperphosphorylated throughout the cycle. These cells, when grown in the presence of vitamin $D_3$, also are characterized by the increased cyclin E to p27$^{KiP1}$ ratio, which would indicate that activation of Cdk2 by cyclin E contributes to abrogation of the vitamin $D_3$-induced arrest in $G_1$. The vitamin $D_3$-induced increase in level of pRb, in this case, appears to be compensated by the increased activity of Cdk2. Analysis of total cellular pRb and its state of phosphorylation at particular phases of the cycle in the cell systems that have cell cycle arrest uncoupled from differentiation may provide additional information about a function of pRb in these processes.

We have shown in Example 1 that mitogenic stimulation of $G_0$ lymphocytes results in rapid phosphorylation of pRb, without a change in cellular level of this protein: proliferating lymphocytes during $G_1$ have total pRB contents similar to that of their counterparts in $G_0$. The cell transition to $G_0$, which is a transient state, thus, unlike the irreversible cell arrest during terminal differentiation, appears to involve only dephosphorylation of pRb, with no change in its cellular content.

Example 3

Multiparameter Flow Cytometric Assay of pRB Phosphorylation in Mechanistic Studies of Cytostatic Arrest of Lymphoma Cells By ONCONASE®

Cells

Human histiocytic lymphoma U-937 cells were purchased from American Type Culture Collection (Manassas, Va., USA) and were maintained in RPMI 1640 medium supplemented with 10% fetal bovine serum, 100 U/ml of penicillin, 100 μg/ml streptomycin and 2mM glutamine (all from Life Technologies, Grand Island, N.Y., USA). The suspension cultures were passaged by re-seeding the cells at a density of $1\times10^5$ cells/ml. The cells were studied during their exponential and asynchronous growth, generally within 72 hours of their re-seeding in medium with fresh serum, before reaching density of $8\times10^5$ cells/ml. The cultures were periodically tested for Mycoplasma infection by staining of cytocentrifuge preparations with the DNA fluorochrome 4,6-diamidino-2-phenylindole (DAPI; Molecular Probes, Eugene, Oreg., USA).

ONCONASE®, provided by Alfacell (Bloomfield, N.J., USA), was diluted in RPMI to the final concentrations as shown in the Results below and figure legends above.

Immunocytochemical Detection of Cyclins and CKIs

Following incubations in the absence or presence of ONCONASE®, the cells were washed with phosphate-buffered saline (PBS) and fixed in suspension in either ice-cold 80% ethanol or absolute methanol for up to 24 h. After fixation, the cells were washed twice with PBS and then suspended in 1 ml of 0.25% Triton X-100 (Sigma, St. Louis, Mo., USA) in PBS on ice for 5 min. The cells were then centrifuged.(300 g, 5 min), the cell pellet suspended 100 µl PBS containing 0.5 µg of the anti-cyclin (or anti-CKI) mAb and 1% bovine serum albumin (BSA; Sigma), and incubated for 2 h at room temperature. Anti-cyclin D3 (clone G107-565); anti-cyclin E (clone HE12); anti-p16$^{INK4A}$ (clone G175-405); and p2$^{WAP1/CIP1}$ (clone SX118) and anti-p27$^{KIP1}$ (clone G173-524) mAbs, all were obtained from PharMingen (San Diego, Calif., USA). After incubation with the respective mAbs the cells were rinsed with PBS containing 1% BSA and incubated with the FITC-conjugated goat anti-mouse IgG antibody (Molecular Probes) diluted 1:30 in PBS containing 1% BSA for 30 min at room temperature in the dark. The cells were washed again, resuspended in 5 µg/ml of propidium iodide (PI; Molecular Probes) and 0.1% RNase A (Sigma) in PBS, and incubated at room temperature for 20 min prior to measurement.

Immunocytochemical Detection of pRB Phosphorylation

The status of phosphorylation of pRB in individual cells was monitored using a combination of anti-pRB antibodies, one specifically detecting underphosphorylated pRB (anti-pRB$^{P-}$ mAb) and another which reacts with total pRB, regardless of its phosphorylation (anti-pRB$^T$ mAb). Briefly, following incubations in the presence or absence of ONCONASE®, the cells were washed with PBS and fixed in suspension in 1% methanol-free formaldehyde in PBS for 15 min on ice. The cells were then washed with PBS and resuspended in ice-cold 80% ethanol for up to 24 h. After fixation the cells were rinsed twice with PBS and then resuspended in 1 ml of 0.25% Triton X-100 in PBS on ice for 5 min. The cells were then centrifuged (300 g, 5 min) the cell pellet resuspended in 100 µl of PBS containing 1% BSA and 0.5 µg/ml of the anti-pRB$^T$ mAb (PharMingen, clone G3-245) conjugated with CYCHROME® and/or with 1 µg/ml of anti-pRB$^{P-}$ mAb (PharMingen, clone G99-549) conjugated with FITC, and incubated for 2 hours at room temperature. The cells were then rinsed with PBS containing 1% BSA and their pRB associated green (anti-pRB$^{P-}$) and red (anti-pRB$^T$) fluorescence was measured by flow cytometry.

Cell Fluorescence Measurements

Cellular fluorescence was measured with the ELITE ESP flow cytometer/cell sorter (Coulter, Miami, Fla., USA) using either argon ion laser (emission at 488 nm) alone or combined with helium-cadmium laser (emitting UV light). In the first case, fluorescence signals were collected using the standard configuration of the flow cytometer (green fluorescence, representing directly or indirectly FITC-labeled antibodies; red fluorescence representing CYCHROME® tagged anti-pRB$^T$ mAb). In the second case, DNA content was analyzed based on DAPI fluorescence (blue emission) excited by UV light, while the anti-pRB$^{P-}$ mAb (FITC) and anti-pRB$^T$ (CYCHROME®) related emission was excited with blue light laser.

Immunoblotting

To reveal specificity of the antibodies that were used, a standard immunoblotting procedure was used on cellular lysates.

Controls

Several controls were performed to confirm the specificity of immunocytochemical detection of the studied proteins. A first control was the use of an isotype-matched irrelevant antibody. Second, MOLT-4 cells, known to have deleted gene coding for p16$^{INK4A}$, were used as control cells for specificity of anti-p16$^{INK4A}$ mAb. The specificity of mAb reacting with underphosphorylated pRB was tested in several laboratories (reviewed in Juan et al., *J. Exp. Cell Res.* 239:104–110 (1998)) and in a separate study using alkaline phosphatase to delete the phosphate moiety from pRB and Cdk inhibitors, such as staurosporine to prevent its phosphorylation. Parallel Western blots were done as well. All experiments were repeated at least three times, yielding essentially identical results.

Results

Figure 11A:
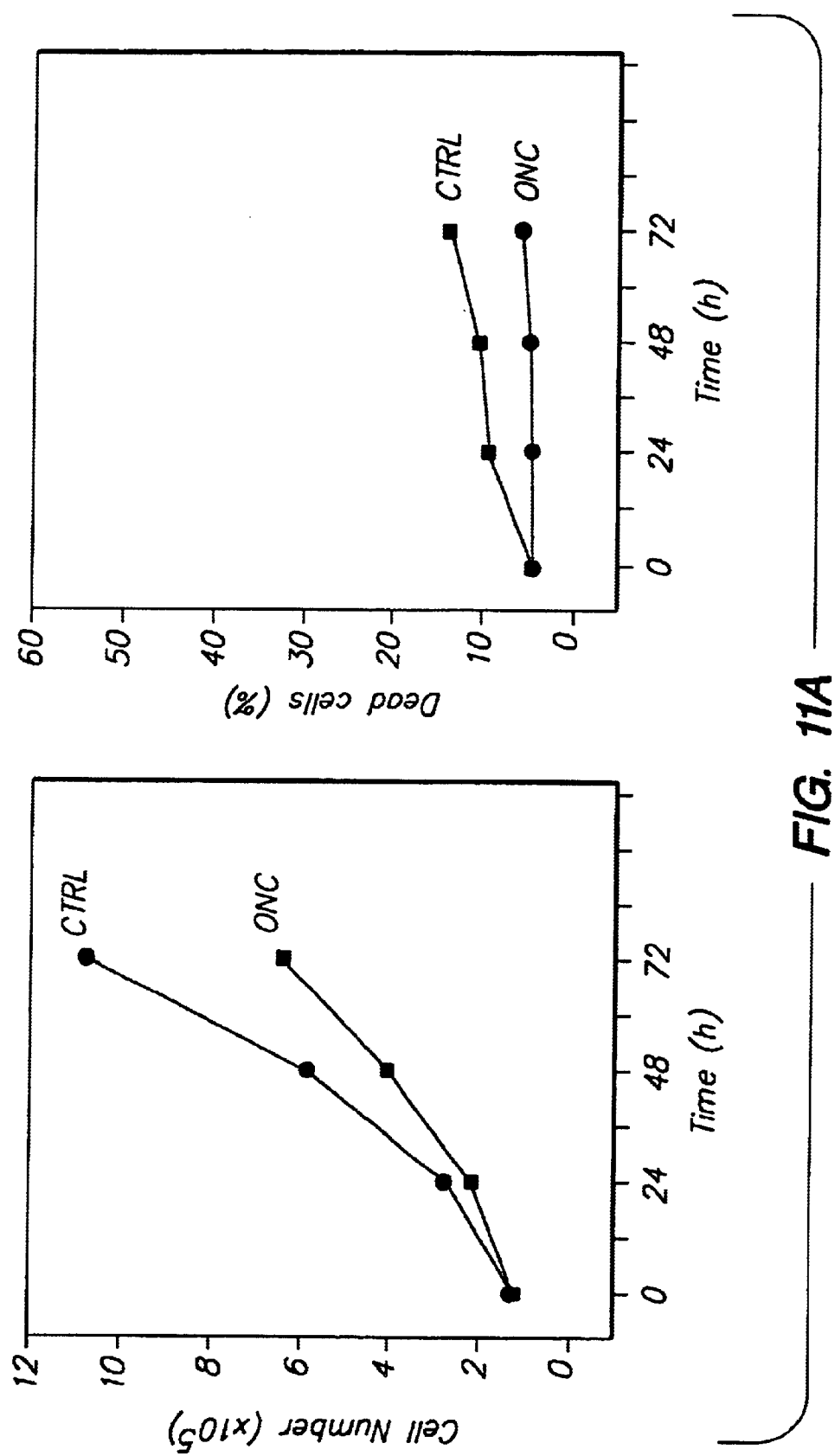
FIG. 11 presents growth and viability curves (a) as well as cell cycle distribution (b) of U937 cells maintained in the absence (CTRL) and presence of 170 nM (2.0μg/ml) ONCONASE® (ONC) for up to 72 h. The percentage of dead cells was estimated based on the trypan blue exclusion test. The percentage of cells in the respective phases was estimated flow cytometrically based on their DNA content. Apoptotic cells (Ap) were recognized as the cells with fractional DNA content (sub-$G_1$), as previously described.

In pilot experiments, we found that 170 nM (20 µg/ml) was the concentration of ONCONASE® at which its cytostatic effect on U937 was apparent while its cytotoxicity, during the initial 72 hours of treatment, remained relatively low. At that drug concentration cell proliferation was suppressed by approximately 50% and fewer than 10% cells were dead (FIG. 11a). This concentration of ONCONASE®, therefore, was used in most experiments throughout this study.

Figure 11B:
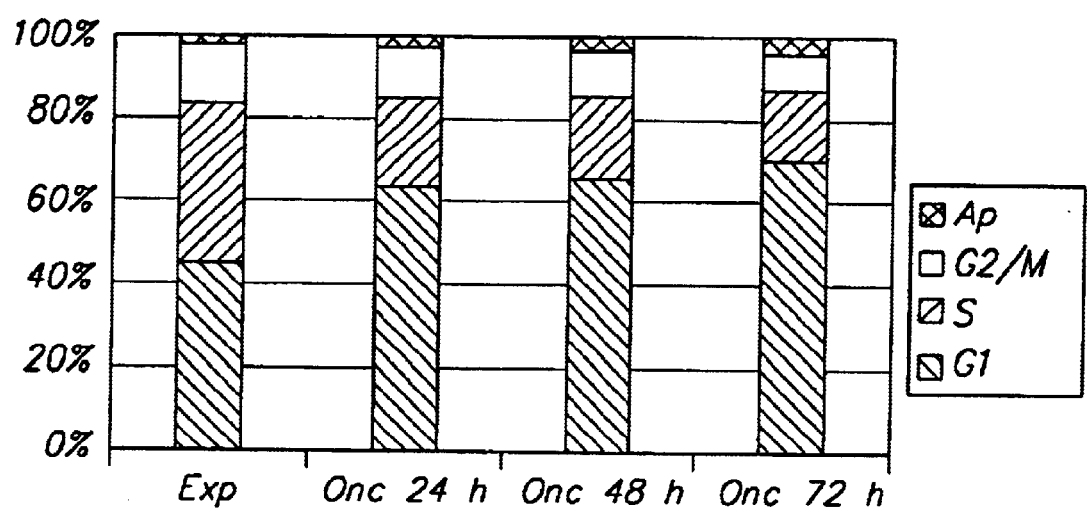

As is evident from the data shown in FIG. 11b, in cultures containing ONCONASE® the proportion of cells in $G_{0/1}$ phase progressively increased, from 47% to nearly 70% after 72 h, concomitant with a decrease in number of S and $G_2$/M cells. A minor increase in percentage of apoptotic cells, from 2 to 6%, also was seen in the ONCONASE®-treated cultures. Apoptotic cells were identified on the cellular DNA content frequency histograms as the cells with fractional DNA content (sub-$G_1$ cell population; Darzynkiewicz et al., *Cytometry* 276:1–20 (1997)). Analysis of their morphology by microscopy, as described before, revealed typical features of apoptosis.

Figure 12A:
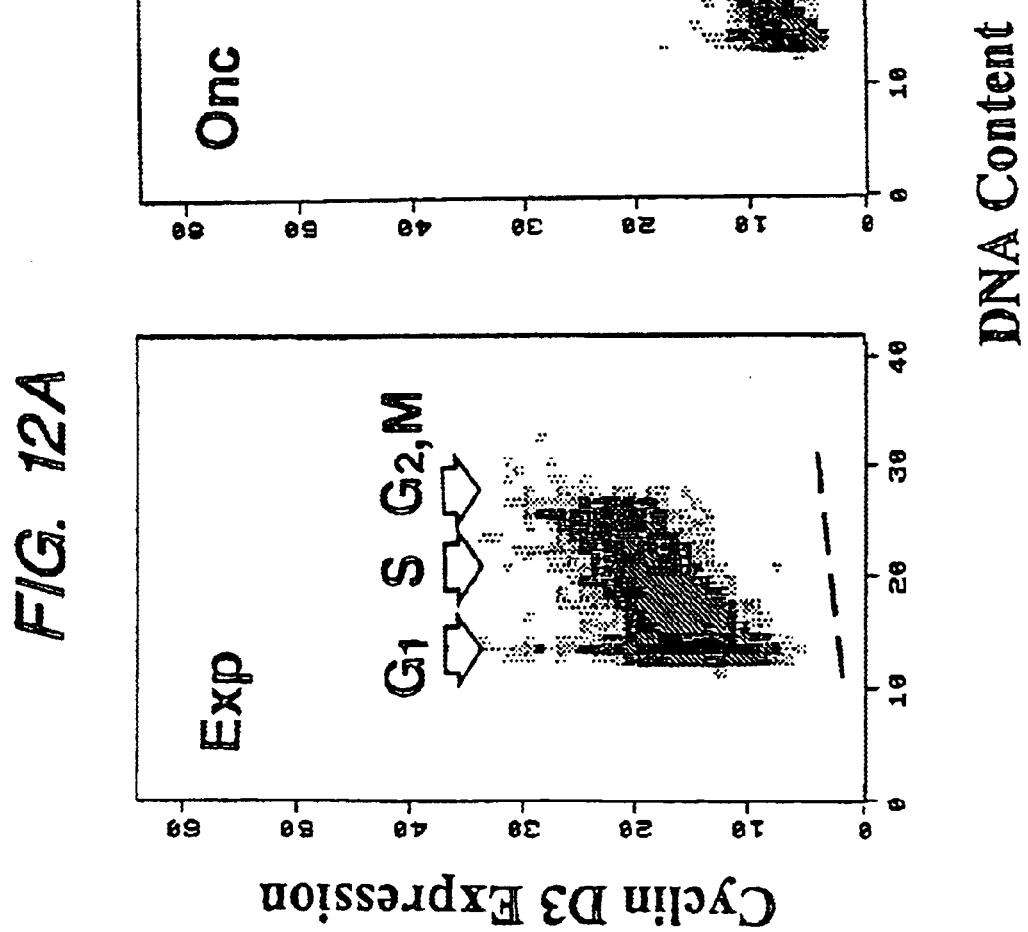
FIG. 12 demonstrates the effect of ONCONASE® on expression of cyclin D3 by U937 cells. Anti-cyclin D3 mAb immunofluorescence in combination with DNA content was measured by multiparameter flow cytometry (a). The cells were growing either in the absence (Exp, exponential growth) or in the presence of 170 nM ONCONASE® for 48 hours (Onc). There were 48%, 38% and 14% of cells in $G_1$, S, and $G_2$/M in Exp culture compared with 64%, 24% and 13% cells in $G_1$, S, and $G_2$/M, respectively, in Onc culture. The scattergrams represent bivariate distributions of the cells with respect to their cyclin D3 vs. DNA content associated fluorescence intensities. The upper level of the isotype-matched control (mean fluorescence +3 standard deviations) is marked in the Exp panel with a dashed line. The bar plots represent the mean FITC (anti-cyclin D3 mAb) fluorescence values (arbitrary units) of the cells in different phases of the cycle (gated based on differences in DNA content as shown in the Exp panel), after subtraction of the background fluorescence, i.e., mean fluorescence of the same cells but stained with isotype-matched control IgG antibody. Western blots (b) show expression of cyclin D3 in control culture and in the culture treated with ONCONASE® 48 h.
Figure 12B:
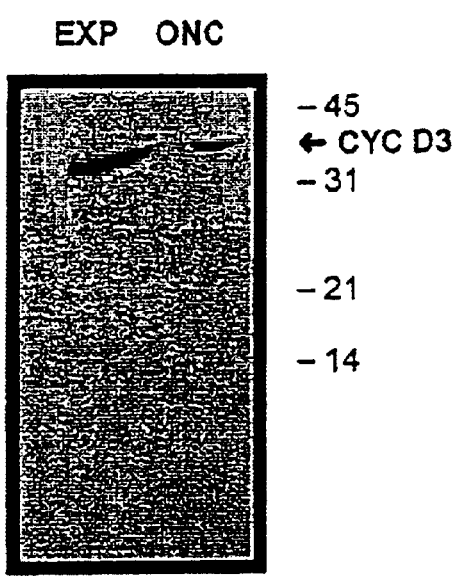

Immunocytochemical detection of any protein, e.g., such as cyclin or CKI, when correlated with cellular DNA content measurement (the latter identifying the cell cycle position) reveals, via analysis of the bivariate distributions such as scattergrams or contour maps, the cycle phase specificity of expression of this protein. Such analysis of cyclin D3 expression in the untreated and ONCONASE® treated U937 cells is presented in FIG. 12. These scattergrams demonstrate that expression of cyclin D3 in exponentially growing untreated cells was unscheduled (FIG. 12; Onc 0 h). That is, in contrast to normal nontumor cells where this protein is transiently expressed in mid-$G_1$ cells and is undetectable in S and $G_2$/M cells, its expression in U937 cells was continuous during the cycle, including S and $G_2$/M phases. The overall level of cyclin D3 was reduced, however, in the cells growing in the presence of ONCONASE®. The decrease by about 20% was already observed after 24 h, but it was more pronounced after 48 hours when the reduction was over 70% (FIG. 12). However, because the range of reduction appeared to be similar regardless of the cycle phase, the pattern of cyclin D3 expression across the cell cycle still remained unscheduled. Analysis of intensities of the bands on the Western blots (FIG. 12b) confirmed the flow cytometric data showing the decrease in expression of cyclin D3 in ONCONASE®-treated cells.

In contrast to cyclin D3, the pattern of cyclin E expression in the untreated U937 cells was similar to that seen in the nontumor cells such as proliferating lymphocytes or fibroblasts, i.e. its maximal expression was on schedule, timely correlated with the cell entrance to S phase. However, unlike cyclin D3, expression of cyclin E was not significantly changed in the cells growing in the presence of ONCONASE® (not shown).

Figure 14B:
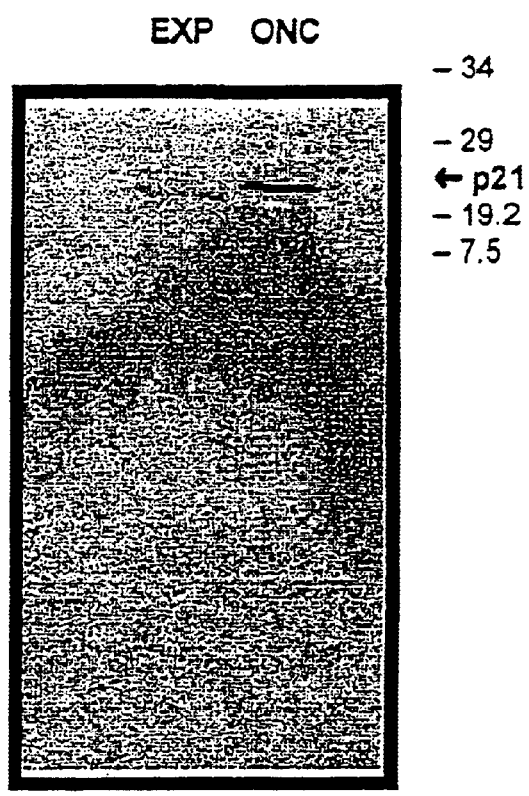
FIG. 14 shows expression of $p21^{WAF1/CIP1}$ in U937 cells growing exponentially (Exp) and in the culture treated with 170 nM ONCONASE® for 72 hours (Onc). The bar plot shows mean anti-$p21^{WAF1/CIP1}$ mAb fluorescence estimated for cells in $G_1$, S and $G_2$/M as described in the legend to FIG. 12. Western blot (B) shows the $p21^{WAF1/CIP1}$ band only in the ONCONASE®-treated cells.
Figure 15B:
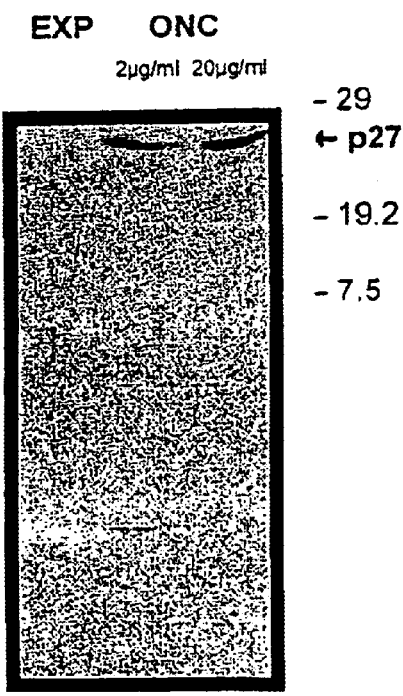
FIG. 15 shows expression of $p27^{KIP1}$ in U937 cells growing exponentially (Exp) and in the culture treated with 170 nM ONCONASE® for 72 hours (Onc). The bar plot shows mean anti-$p27^{KIP1}$-mAb fluorescence estimated for cell in $G_1$, S and $G_2$/M as described in the legend to FIG. 12. Western blot analysis (b) of this protein failed to detect its presence in the cells growing exponentially in the absence of ONCONASE® (Exp), but revealed strong bands after incubation of cells with 17 and 170 nM ONCONASE® (Onc) for 72 h.
Figure 13:
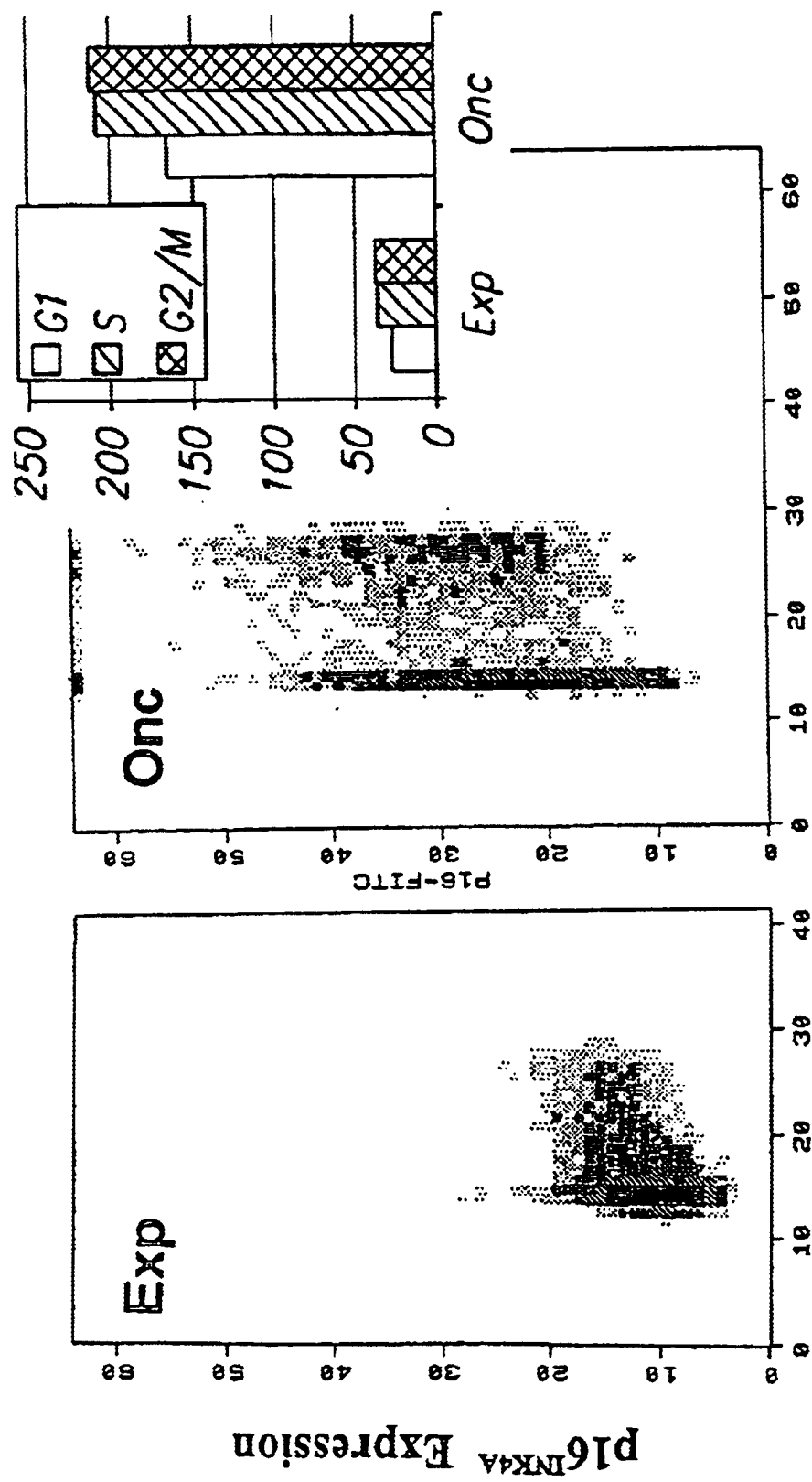
FIG. 13 shows expression of $p16^{INK4A}$ in U937 cells growing exponentially (Exp) and in the culture treated with 170 nM ONCONASE® for 72 hours (Onc). The bar plot shows mean anti-$p16^{INK4A}$ fluorescence estimated for cells in $G_1$ S and $G_2$/M, as described in the legend to FIG. 12. Proportions of cells in different phases of the cycle were the same as in FIG. 12.
Figure 14A:
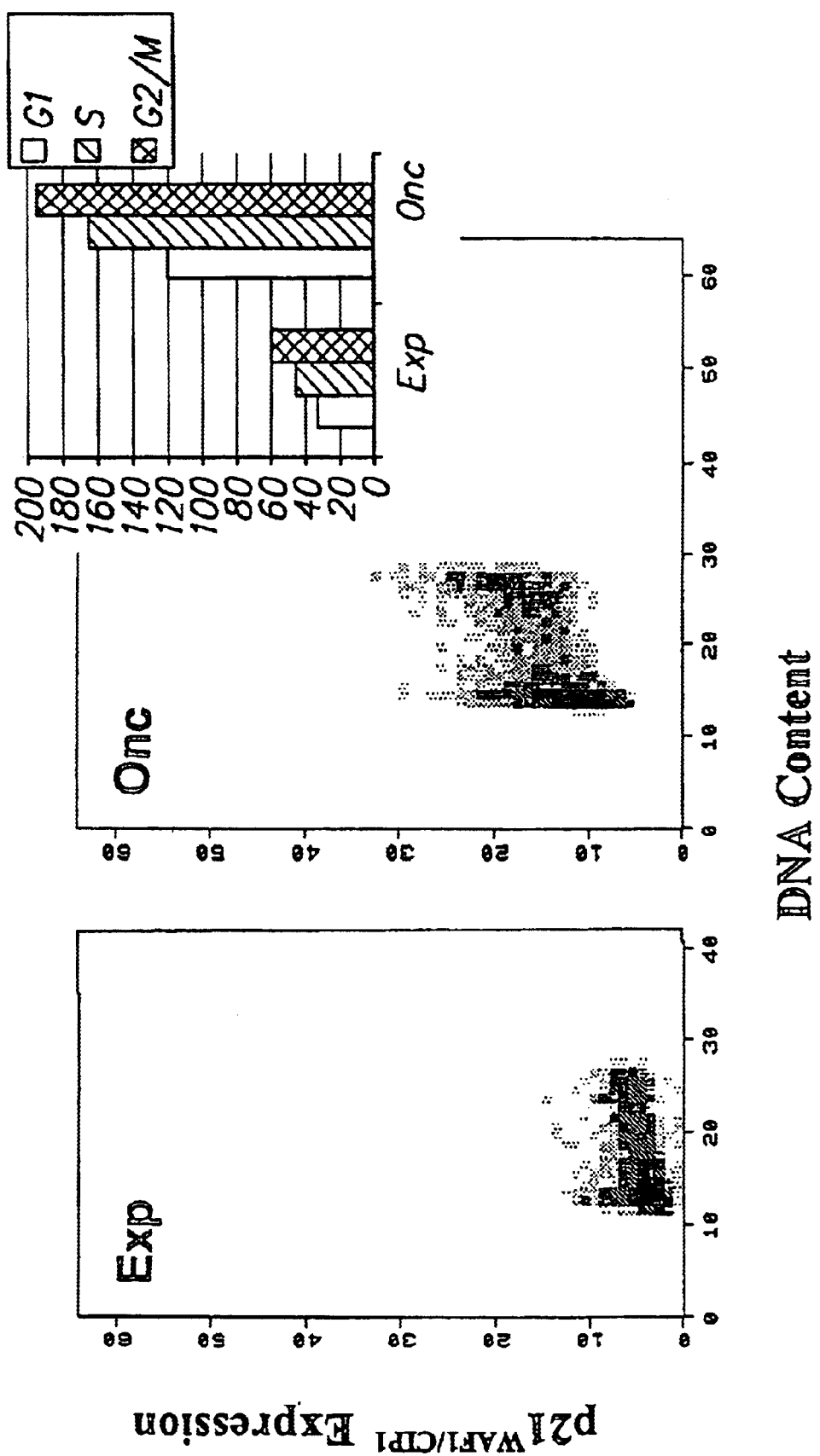
Figure 15A:
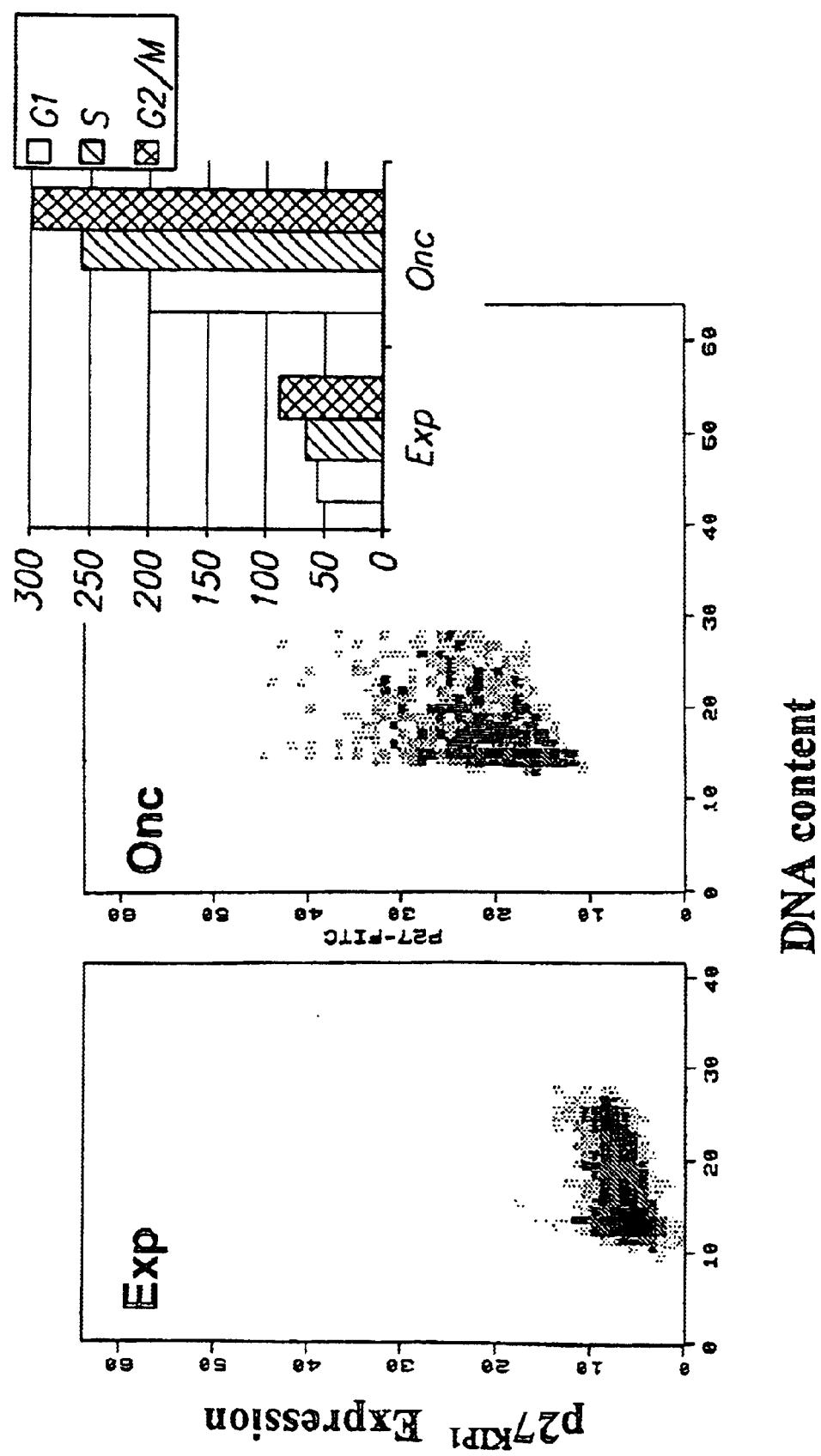

Expression of each of the CKIs—$p16^{INK4A}$, $p21^{WAF1/CIP1}$ and $p27^{KIP1}$—was markedly elevated in the cells growing in the presence of ONCONASE® (FIGS. 13, 14 and 15). The greatest increase was observed for $p16^{INK4A}$, whose level rose over six-fold after 72 hours incubation with the drug. Over four-fold increase was observed for $p27^{KIP1}$ and $p21^{WAF1/CIP1}$. Similarly as in the case of cyclin D3, the increase was not specific to any particular cell cycle phase but was of comparable degree across the whole cell cycle, for each of the studied CKIs.

Figure 16:
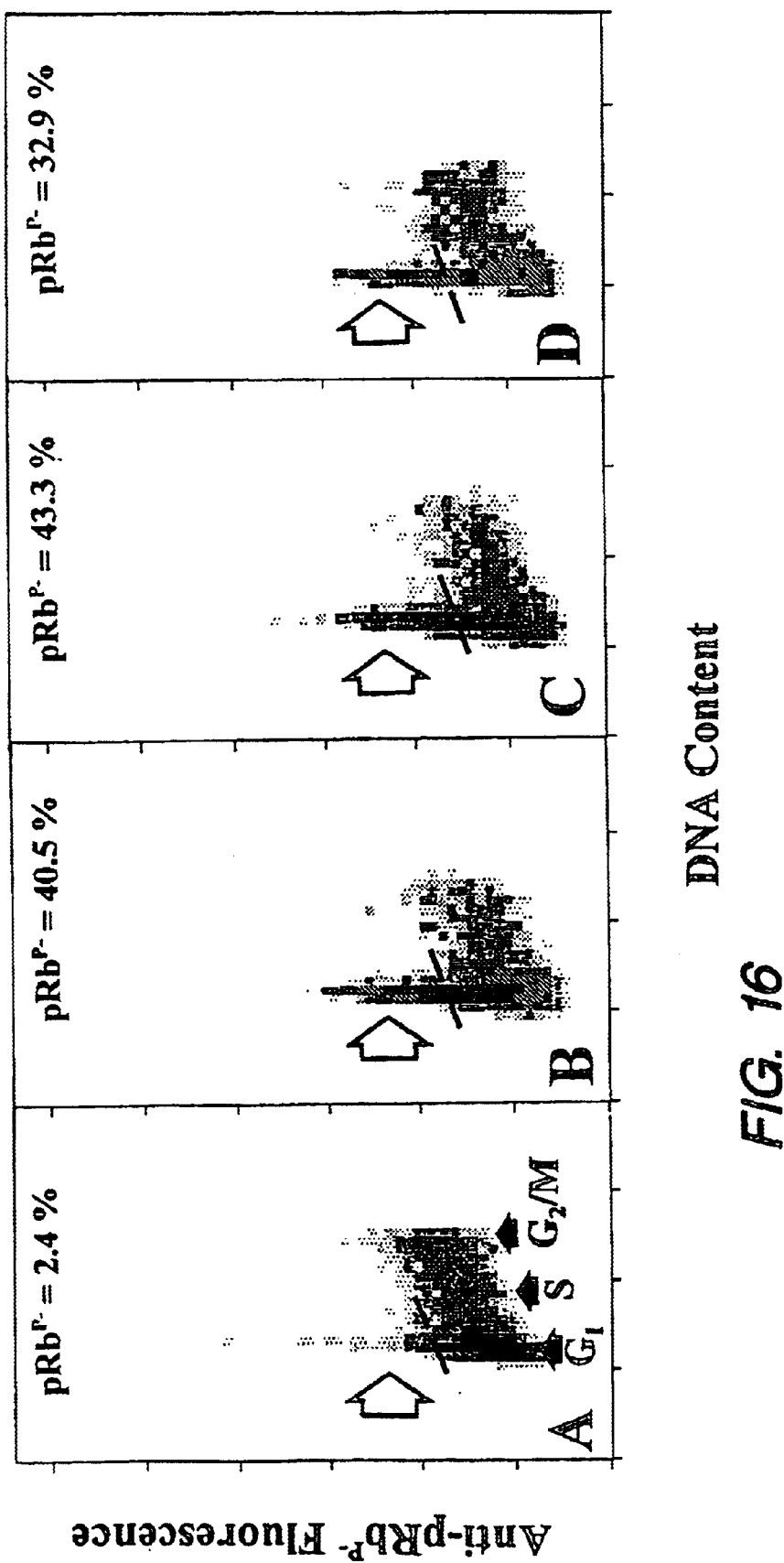
FIG. 16 shows detection of U937 cells having underphosphorylated pRB in exponentially growing control culture (panel a) and in the cultures treated with 170 nM ONCONASE® for 48 hours (panel b) and 72 hours (panel c). Also shown are cells from the culture at higher cell density (>$10^6$ cells/ml) where proliferation declined because of cell crowding (d). The cells reacting with anti-$pRB^{P-}$ were in $G_{0/1}$ phase (open arrows). The dashed line indicates the upper level of background fluorescence, i.e. of the cells pretreated with alkaline phosphatase. The percentage of cells reacting with anti-$pRB^{P-}$ mAb was increased in the ONCONASE®-treated and crowded cultures compared to the control. No significant changes in expression of pRB detected by the antibody that reacts with this protein regardless of its phosphorylation status (anti-$pRB^T$) were observed between ONCONASE®-treated and control cells (not shown).

The status of pRB phosphorylation in U937 cells growing in the absence and presence of ONCONASE® was monitored immunocytochemically using two anti-pRB antibodies, one which reacts with this protein regardless of the state of its phosphorylation and thus detects total pRB (anti-pRB$^T$), and another which binds specifically to underphosphorylated pRB and is not reactive with the phosphorylated form of this protein (anti-pRB$^{P-}$, FIG. 16).

Incubation of cells with ONCONASE® had no effect on total pRB, as detected by antibody which reacts with this protein regardless of its phosphorylation status (anti-pRB$^T$; data no shown). The effect, however, was apparent in binding the anti-pRB$^{P-}$ mAb (FIG. 16). In a population of exponentially growing cells from the control culture relatively few (2.4%) cells reacted with anti-pRB$^{P-}$ mAb and essentially all these cells had a $G_{0/1}$ DNA content; the cells in S, $G_2$/M as well as most cells in $G_{0/1}$ phase were anti-pRB$^{P-}$ negative. The proportion of cells stainable with anti-pRB$^{P-}$ was increased to 40.5 and 43.3% in cultures treated with ONCONASE® for 48 and 72 h, respectively. As an additional control served the cells from the culture which was maintained without re-seeding and medium change until it reached a density over $10^6$ cells/ml (FIG. 16d). The cells become arrested in $G_{0/1}$ in this culture as well, and similar to the ONCONASE®-treated cultures maintained at lower cell density, had also increased proportion of $G_{0/1}$ cells reacting with anti-pRB$^{P-}$.

Discussion

In this Example, changes in expression of the cell cycle associated proteins and pRb phosphorylation have been investigated using multiparameter flow cytometry. This approach offers several advantages and provides information complementary to the standard analysis by Western blotting. The greatest advantage is the ability to detect intercellular variability and to correlate expression of the studied proteins with the cell cycle position, without requiring synchronization of the culture. Synchronization of tumor-transformed cells, which requires use of the agents suppressing DNA replication, induces significant growth imbalance which leads to experimental bias, especially in analysis of the components of the cell cycle regulatory machinery.

Progression of U937 cells through the cell cycle was perturbed in the presence of ONCONASE® which manifested as an accumulation of cells in $G_{0/1}$. The cytostatic effect occurred with a delay and significant accumulation of $G_{0/1}$ cells was seen only after 24 hours of incubation with the drug. The observed increase in proportion of cells in $G_{0/1}$ confirmed our earlier findings on other types of cells treated with ONCONASE®, and indicated that in the presence of this drug, U937 cells become progressively arrested in $G_{0/1}$. The cytotoxic effect, which becomes more pronounced after prolonged incubation with ONCONASE® (over 72 hours), and manifests as apoptotic cell death, was not a subject of the present study.

Concomitant with cell arrest in $G_{0/1}$, the ONCONASE®-treated cells exhibited a decrease in expression of cyclin D3 and increased levels of all the three CKIs. These changes in cyclin D3 or CKIs expression characterized all ONCONASE®-treated cells, regardless of their phase in the cycle. Only the $G_{0/1}$ arrested cells, however, developed the ability to bind anti-pRb$^{P-}$ mAb. These data suggest that during cell growth in the presence of ONCONASE®, downregulation of cyclin D3, upregulation of the $p16^{INK4A}$ and $p21^{WAF1/CIP1}$ and induction of $p27^{KIP1}$ took place when the cells were still progressing through the cycle. Reactivity of the $G_{0/1}$ arrested cells with anti-pRb$^{P-}$ mAb indicates that pRb was underphosphorylated in these cells, i.e. the cells become arrested prior to, or at the restriction point in $G_1$ which is controlled by phosphorylation of pRb. Since no significant changes were observed in expression of cyclin E, and since pRb of the cells which progressed through S and $G_2$/M were phosphorylated, it is likely that once the cells passed the $G_{0/1}$ restriction point their progression through the remainder of the cycle was unaffected in the presence of ONCONASE®.

Each of the observed changes in expression of cyclin D3 or CKIs alone may be held accountable for the suppression of pRb phosphorylation leading to cell arrest in $G_{0/1}$. Thus, the D-type cyclins are activators of Cdk4/6, the protein kinases which specifically target pRb for phosphorylation during $G_1$. Cyclins of the D type are tissue-specific and cyclins D2 and D3 are expressed in hematopoietic cells. $p21^{WAF1/CIP1}$ binds stoichiometrically to multiple Cdks blocking activation of the Cdk/cyclin complexes and suppressing their ability to phosphorylate substrates, notably pRb. This inhibitor can be induced either via activation of the tumor suppressor gene p53, or independently of p53, by two growth suppressing factors, transforming growth factor β (TGF-β) and interferon regulatory factor 1 (RF-1). The interaction between interferons and $p21^{WAF1/CIP}$ also involves signal transducing activators of transcription (STA1) proteins since one of these proteins (STAT1) induces expression of this CKI. It is likely that suppression of cell growth by interferons is mediated via induction of $p21^{WAF1/CIP1}$. Similar to $p21^{WAF1/CIP1}$, $p27^{KIP1}$ binds to the Cdk/cyclin complexes and targets multiple Cdks. Also, as $p21^{WAF1/CIP1}$, it mediates TGF-β activity via affecting pRb phosphorylation and arresting cells in $G_1$ and S. It is not surprising, therefore, that $p_{27}$KZP1 deficient mice show similarity to retinoblastoma gene-deficient mice, both characterized by hyperplasia of many organs having pituitary dysfunction.

Unlike the two first CKIs, the INK family member $p16^{INK4A}$ specifically binds to Cdk4 (rather than to the Cdk/cyclin complex) and inhibits activity of Cdk4/cyclin D. A vast body of literature indicates that overexpression or ectopic expression of $p16^{INK4A}$ prevents pRb phosphorylation. ONCONASE®, by downregulating expression of cyclin D3 as well as enhancing expression of each of the three CKIs, has multiple intermediate pathways to prevent pRb phosphorylation in $G_1$.

A common feature of tumor cells is the abrogation of cell cycle checkpoints, in particular the G1 checkpoint, either by aberrant expression of positive regulators (cyclins and Cdks), loss of negative regulators (CKIs), or both. All components of the cell cycle regulatory machinery whose expression, as shown in the present study, was modulated by ONCONASE®, are frequently abnormal or deleted in cancer. Thus, aberrant expression or deletion of the gene coding for $p16^{INK4A}$, the so-called multiple tumor suppressor-1 (MTS1), which is located on chromosome 9p21, is a common feature in a variety of tumors, in particular melanomas, acute lymphocytic leukemias, gliomas and mesotheliomas. The gene encoding $p27^{KIP1}$ is located on chromosome 12p13 and this chromosome fragment is aberrant in several hematological tumors and myeloproliferative disorders. The gene of $p21^{WAF1/CIP1}$ present on chromosome 6p21 appears to be involved in various tumors by virtue of its downstream of p53 functional role. The antitumor potency of ONCONASE®, may thus be related to its ability to substitute for loss of a function of each of the above gene products in terms of prevention of pRb phosphorylation.

ONCONASE® is a novel drug and its mechanism of action is still an enigma. The ribonuclease activity of ONCONASE® appears to be a prerequisite for its cytostatic and cytotoxic properties. This protein is present in amphibian eggs and early embryos where its physiological role is unknown. Since fertilized eggs do divide one may expect that some inhibitor of enzymatic activity of ONCONASE® is present within the eggs. It is difficult to visualize the mechanism by which this ribonuclease may selectively affect the cell cycle regulatory molecules as presently observed, namely downregulate expression of cyclin D3, have no effect on cyclin E, and augment expression of all three CKIs. The mechanism proposed in earlier studies, via degradation of tRNA, cannot be selective enough to explain the present findings, especially enhancement of CKIs expression. It was also puzzling to observe that all three CKIs were upregulated by ONCONASE®.

It is tempting to speculate that some RNA or ribonuclein complex which has regulatory function may be present in the cell and that this RNA may be a target of ONCONASE®. Its degradation may trigger a specific response in terms of modulation of the cell cycle progression, as presently seen. An intriguing possibility is that activity of the double-stranded (ds) RNA-dependent protein kinase (PKR), the enzyme which phosphorylates IKB and thereby activates the ubiquitous transcription fact NFkB, may be affected by ONCONASE® via degradation of the dsRNA regulatory of this kinase. Among a multitude of genes activated by NFkB there are genes which regulate cell growth. It is possible, therefore, that dsRNA is one of the ONCONASE® targets and its degradation results in inhibition of PKR which may lead to suppression of cell proliferation. In parallel to its cytostatic effect, ONCONASE® induces cell apoptosis. The apoptotic pathway can also be linked with ONCONASE® via NFkB, since interference with activation of this transcription factor is known to prevent expression of the cell survival factors and enhances sensitivity to apoptosis. Results of our recent experiments, utilizing the cells with defective NFkB pathway to study effects of ONCONASE®, suggest involvement of this pathway in modulation of ONCONASE® cytotoxicity.

All patents, patent publications, and other published references mentioned herein are hereby incorporated by reference in their entirety as if each had been individually and specifically incorporated by reference herein. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A method for determining the relative intracellular conformational states of a protein, wherein said conformational states result from the phosphorylation state of said protein, comprising:

permeabilizing said cell;

contacting said cell with a first antibody, said first antibody specific for a first conformation of said protein, and a second antibody, said second antibody specific for at least one other conformation of said protein, said first and second antibodies being distinguishably labeled;

detecting intracellular binding of each of said antibodies concurrently by said cell by detecting labels of the first and second antibodies; and determining the relative binding thereof.

2. The method of claim 1, further comprising the antecedent step of fixing said cell.

3. The method of claim 1, wherein said labels are fluorophore and said fluorophores are distinguishable by laser cytometer.

4. The method of claim 3, wherein said laser cytometer is a flow cytometer, and said fluorophores are flow cytometrically distinguishable.

5. The method of claim 3, wherein one of said fluorophores is fluorescein isothiocyanate (FITC).

6. The method of claim 3, wherein one of said fluorophores is phycocrythrin (PE).

7. The method of claim 3, wherein one of said fluorophores is peridinium chlorophyll protein (PerCP).

8. The method of claim 3, wherein one of said fluorophores is PE-CY5 tandem fluorophore.

9. The method of claim 3, wherein one of said fluorophores is PerCP-CY5.5 tandem fluorophore.

10. The method of claim 1, further comprising the step of contacting said cell will a fluorescent mucleic acid stain, and detection the binding to DNA of said stain concurrently with detecting the binding to said protein of said first and second antibody.

11. The method of claim 10, wherein said fluorescent mucleic acid stain is selected from the group consisting of 4,6-diamidino-2-phenyl indole (DAPI) and propidium iodide (PI).

12. The method of claim 1, further comprising contacting said cell with a third antibody, said third antibody specific for a second protein and wherein said first, second and third antibody are distinguishably labeled, and then detecting the concurrent binding of each of said antibodies to said cell by detecting labels of said first, second and third antibody.

13. The method of claim 1 wherein said cell is a lymphocyte and said labels are fluorophores.

14. The method of claim 1 wherein said first antibody and said second antibody bind to a first and second epitope respectively, and wherein said first and second epitopes are not differentially phosphorylated.

15. The method of claim 1, wherein said protein is retinoblastoma susceptibility gene protein (pRB).

16. The method of claim 15, wherein said first antibody is specific for a conformation assumed by the hypophosphorylated form of pRB.

17. The method of claim 16, said second antibody is specific for all functional conformation of pRB.

18. The method of claim 15, wherein said cell is a human cell.

19. The method of claim 15, further comprising contacting said cell with a third antibody, said third antibody specific for a second and wherein said first, second and third antibody are distinguishably labeled, and then detecting the concurrent binding of each of said antibodies to said cell by detecting labels of said first, second and third antibody.

20. The method of claim 19, wherein said second protein is a cyclin dependent kinase inhibitor.

21. The method of claim 20, wherein said cyclin dependent kinase inhibitor is selected from the group consisting of: $p15^{INK4b}$, $p16^{INK4a}$, $p18^{INK4}$, $p19^{INK4c}$, $p21^{WAF1/CIP1}$, and $p27^{Kip1}$.

22. The method of claim 21, wherein said cyclin dependent kinase inhibitor is $p16^{INK4a}$.

23. The method of claim 19, wherein said second protein is a cyclin.

24. The method of claim 23, wherein said cyclin is selected from the group consisting of cyclin A, cyclin B1, cyclin C, cyclin D1, cyclin D2, cyclin D3, cyclin E, cyclin F, cyclin G, cyclin H, cyclin I, and cyclin K.

25. The method of claim 24, wherein said cyclin is cyclin D3.

26. The method of claim 19, wherein said second protein is a cyclin dependent kinase.

27. The method of claim 26, wherein said cyclin dependent kinase is selected from the group consisting of: Cdk1, Cdk2, Cdk3, Cdk4, Cdk5, Cdk6, Cdk7 and Cdk8.

28. The method of claim 27, wherein said cyclin dependent kinase is Cdk4.

29. The method of claim 27, wherein said cyclin dependent kinase is Cdk6.

30. A method for determining the relative intracellular phosphorylation states of a protein, comprising:

permeabilizing said cell;

contacting said cell with a first antibody, said first antibody specific for a first phosphorylation state of said protein, and a second antibody, said second antibody specific for at least one other phosphorylation state of said protein, and first and second antibodies being distinguishably labeled;

detecting intracellular binding of each of said antibodies concurrently by said cell by detecting labels of the first and second antibodies; and determining the relative binding thereof.

31. The method of claim 30, further comprising the antecedent step of fixing said cell.

32. The method of claim 30, wherein said labels are fluorophores and said fluorophores are distinguishable by a laser cytometer.

33. The method of claim 32, wherein said laser cytometer is a flow cytometer, and said fluorophores are flow cytometrically distinguishable.

34. The method of claim 32, wherein one of said fluorophores is selected from the group consisting of fluorescein isothiocyanate (FITC), phycoerythrin (PE), peridinium chlorophyll protein (PerCP), PE-CY5 tandem fluorophore, and PerCP-CY5.5 tandem fluorophore.

35. The method of claim 30, further comprising the step of contacting said cell with a fluorescent nucleic acid stain, and then detecting the binding to DNA of said stain concurrently with detecting the binding to said protein of said first and second antibody.

36. The method of claim 35, wherein said fluorescent nucleic acid stain is selected from the group consisting of 4,6-diamidino-2-phenyl indole (DAPI) and propidium iodide (PI).

37. The method of claim 30, further comprising contacting said cell with a third antibody, said third antibody specific for a second protein and wherein said first, second and third antibody are distinguishably labeled, and then detecting the concurrent binding of each of said antibodies to said cell by detecting labels of said first, second and third antibody.

* * * * *

UNITED STATES PATENT AND TRADEMARK OFFICE
CERTIFICATE OF CORRECTION

PATENT NO.    : 6,821,740 B2
DATED         : November 23, 2004
INVENTOR(S)   : Darzynkiewicz et al.

It is certified that error appears in the above-identified patent and that said Letters Patent is hereby corrected as shown below:

Column 5,
Following line 61, insert the following text:

--Additional embodiments of the invention are as follows:
the ability to reveal cell heterogeneity as a function of pRb phosphorylation, for example with respect to solid tumors, leukemias, and other proliferative disorders;
the ability to reveal the presence of cell subpopulations differing in the degree of pRb phosphorylation (tumor heterogeneity) by looking at the phosphorylation of Rb in tumor tissue as a whole;
the ability to detect rare cells within large cell populations that have either unphosphorylated and/or phosphorylated pRb, and differ from the population as a whole. Such differences may be in the pRb phosphorylation status or in some other marker;
the ability to reveal kinetics of pRb phosphorylation within individual cells, for example to identify that pRb phosphorylation in mitogenetically stimulated lymphocytes was rapid, quantum-like, affecting all pRb within individual cells rather than proceeding stepwise over an extended period;
the ability to correlate the status of pRb phosphorylation with cell cycle position without the need to synchronize cells in the study population;
the ability to correlate the status of pRb phosphorylation with cell phenotype;
the ability to correlate the status of pRb phosphorylation with any other cellular component which can be detected immunocytochemically, e.g. cyclins, inhibitors of cyclins-dependent kinase inhibitors, proliferation-associated antigens, etc., such determinations may be made at the same time as the pRb measurement as in multi-color flow cytometry or may be made sequentially on sorted or immobilized cells;
the ability to correlate the status of pRb phosphorylation with DNA replication, within the individual cell, by immunocytochemically detecting BrdU incorporation in the same cells in which pRb phosphorylation is measured;
an antibody which recognizes the unphosphorylated form of Rb;
a new method for monitoring pRb phosphorylation in individual cells and correlate the presence, absence or ratio of pRb phosphorylated to unphosphorylated, it with the cell cycle position;
the use of two antibodies, one which preferentially recognizes the phosphorylated form and one which recognizes the unphosphorylated form, to determine the proportion of a given molecule which is phosphorylated (e.g. Rb/pRb);
the use of antibodies to differentiate phosphorylated forms of the same protein, which would be useful for example in determining the biologically significant change in state of the cell itself, this would not be dependent on the phosphorylation site;
an agent recognizing the SV40 large T binding region on Rb for purposes of screening antibodies or anti-tumor drugs;
various diagnostic and prognostic applications with respect to monitoring tumors, as a predictor of tumor proliferation;

UNITED STATES PATENT AND TRADEMARK OFFICE
CERTIFICATE OF CORRECTION

PATENT NO. : 6,821,740 B2
DATED : November 23, 2004
INVENTOR(S) : Darzynkiewicz et al.

It is certified that error appears in the above-identified patent and that said Letters Patent is hereby corrected as shown below:

Column 5 (cont'd),
use of the variable region structure of the underphosphorylated Rb specific antibody as a model for drug screening, evaluation, or design; as a model for an inhibitor of Rb; as an agent useful in gene therapy;
an antibody that recognizes status of phosphorylation of a protein based in change in conformation of this protein resulting from its phosphorylation or dephosphorylation rather than directly requiring phosphorylation or dephosphorylation of the epitope itself. Thus, the site(s) of phosphorylation is (are) not an epitope itself;
an antibody which identifies non-cycling ($G_0$) cells. --

Column 36,
Line 42, delete "detection" and insert therefor -- then detecting --.
Line 46, delete "mucleic" and insert therefor -- nucleic --.
Line 67, delete "conformation" and insert therefor -- conformations --.

Column 37,
Line 5, after "specific for a second" insert -- protein --.

Column 38,
Line 2, after "said protein," delete "and" and insert therefor -- said --.

Signed and Sealed this

Twenty-fifth Day of October, 2005

JON W. DUDAS
*Director of the United States Patent and Trademark Office*